(12) United States Patent
Hafeman et al.

(10) Patent No.: US 6,339,472 B1
(45) Date of Patent: *Jan. 15, 2002

(54) DETERMINATION OF LIGHT ABSORPTION PATHLENGTH IN A VERTICAL-BEAM PHOTOMETER

(76) Inventors: Dean G. Hafeman, 1350 Buckingham Way, Hillsborough, CA (US) 94010; Calvin T. Chow, 45 Santa Maria, Portola Valley, CA (US) 94028

( * ) Notice: Subject to any disclaimer, the term of this patent is extended or adjusted under 35 U.S.C. 154(b) by 0 days.

This patent is subject to a terminal disclaimer.

(21) Appl. No.: 09/557,750
(22) Filed: Apr. 25, 2000

Related U.S. Application Data

(62) Division of application No. 09/220,177, filed on Dec. 23, 1998.

(51) Int. Cl.[7] .............................................. G01N 21/00
(52) U.S. Cl. ....................................... 356/433; 356/436
(58) Field of Search .................... 356/440, 442, 356/434, 436, 319–320, 414, 418–419; 250/343, 344, 373, 339.05, 339.12

(56) References Cited

U.S. PATENT DOCUMENTS

| | | | | |
|---|---|---|---|---|
| 3,902,812 A | * | 9/1975 | Honkawa | |
| 5,298,978 A | * | 3/1994 | Curtis et al. | 356/435 |
| 5,959,738 A | * | 9/1999 | Hafeman et al. | 356/442 |

FOREIGN PATENT DOCUMENTS

| | | | |
|---|---|---|---|
| JP | 60-39533 | * | 3/1985 |

* cited by examiner

Primary Examiner—Hoa Q. Pham
(74) Attorney, Agent, or Firm—McDonney Boehnen Hulbert & Berghoff

(57) ABSTRACT

Disclosed are photometric methods and devices for determining optical pathlength of liquid samples containing analytes dissolved or suspended in a solvent. The methods and devices rely on determining a relationship between the light absorption properties of the solvent and the optical pathlength of liquid samples containing the solvent. This relationship is used to establish the optical pathlength for samples containing an unknown concentration of analyte but having similar solvent composition. Further disclosed are methods and devices for determining the concentration of analyte in such samples where both the optical pathlength and the concentration of analyte are unknown. The methods and devices rely on separately determining, at different wavelengths of light, light absorption by the solvent and light absorption by the analyte. Light absorption by the analyte, together with the optical pathlength so determined, is used to calculate the concentration of the analyte. Devices for carrying out the methods particularly advantageously include vertical-beam photometers containing samples disposed within the wells of multi-assay plates, wherein the photometer is able to monitor light absorption of each sample at multiple wavelengths, including in the visible or UV-visible region of the spectrum, as well as in the near-infrared region of the electromagnetic spectrum. Novel photometer devices are described which automatically determine the concentration of analytes in such multi-assay plates directly without employing a standard curve.

5 Claims, 9 Drawing Sheets

DETERMINATION OF LIGHT ABSORPTION PATHLENGTH IN A VERTICAL-BEAM PHOTOMETER

This is a Divisional of prior application Ser. No. 09/220, 177 filed Dec. 23, 1998.

BACKGROUND OF THE INVENTION

1. Field of the Invention

This invention relates to the field of photometry. In particular, the invention relates to spectrophotometric methods and apparatus capable of determining the light absorption pathlength for various samples to be analyzed with a spectrophotometer.

2. Description of the Related Art

The problem of an undefined light absorption pathlength in vertical-beam photometers has existed since the advent of vertical-beam photometers, i.e., for over 20 years. Substantial errors in determination by vertical-beam photometry of either relative optical pathlength or the concentration of analytes in a solvent contained in a sample-retaining device of unknown optical pathlength by prior art methods occur because of 1) substantial variation in solvent temperature, 2) substantial variation in the solvent composition, 3) substantial presence of materials in the samples which absorb light in the wavelength region where the optical pathlength of the solvent is being monitored and 4) optical aberrations which occur upon passing analysis light though the variable curved meniscus of samples having a liquid-gas interface.

Photometry is a common measurement technique employed to monitor optical characteristics of samples. Customarily, samples contain an analyte species dissolved in a solvent at an unknown concentration. The concentration of the analyte in a sample may be determined by using a photometric device to measure the fraction of light absorbed by the sample at a specific wavelength ($\lambda$). The value of $\lambda$ is usually chosen to be near the wavelength of light where the analyte absorbs maximally. According to the Beer-Lambert law, equation 1, absorbance is determined as follows:

$$\text{Absorbance } (A_\lambda) = \log\frac{I_o}{I} = \varepsilon_\lambda \cdot l \cdot C \quad (1)$$

where $I_O$ is the incident radiation intensity, I is the intensity of light emerging from the sample, $\epsilon_\lambda$ is the molar extinction coefficient of the analyte dissolved in the solvent, is the light absorption pathlength, and C is the concentration of absorbing analyte in the solvent. The value of I customarily is measured with a photometric apparatus, such as a photometer or spectrophotometer, equipped with a fixed light path sample-retaining device called a cuvette, such as a 1 cm light absorption pathlength cuvette. The sample-retaining device contains a sample comprised of analyte dissolved in a solvent. The value of $I_O$ is ordinarily measured with the same system (photometric apparatus, sample-retaining device and solvent except that no analyte is present in the solvent. Alternatively, $I_O$ may be measured in the absence of both the sample and the sample-retaining device (this value of $I_O$ is called an "air blank"). When an "air blank" is employed, a separate $A_\lambda$ measurement of the solvent and sample-retaining device gives a "solvent blank" absorbance value. A "corrected absorbance" value related to absorbance of the analyte is then obtained by subtracting the "solvent blank" from each absorbance measurement made on the samples comprised of analyte dissolved in solvent and contained in the sample-retaining device. These two alternative procedures and combinations thereof give mathematically equivalent results. Absorbance measurements made by either procedure allows unknown concentrations of the analyte to be determined by calculation according to Eq. 1, provided that $\epsilon\lambda$ and l are known.

A spectrophotometer is a photometric apparatus which employs an adjustable means to pre-select a desired portion of the electromagnetic spectrum as incident radiation. Usually spectrophotometers employ a monochrometer having a dispersive means, such as a prism or diffraction-grating, to provide continuously selectable, narrow, bands of light centered about the desired wavelength $\lambda$. Most conventional photometers and spectrophotometers employ a horizontal light beam that traverses the liquid sample so as to avoid passing through a liquid-gas interface that is typically above the sample. With such horizontal-beam photometers, the geometry and optical pathlength within the sample is fixed for any given cuvette. Cuvettes for visible and ultraviolet light absorption measurements customarily have a 1 cm pathlength. Cuvettes with pathlengths between 0.1 cm and 10 cm are also common, however. With any such fixed pathlength cuvette in a horizontal-beam photometers, unknown concentrations C of the analytes may be calculated from absorbance measurements provided that the values of $\epsilon_\lambda$ and l are known.

When either $\epsilon_\lambda$ and l is not known, values of C may be determined readily by employing known concentrations of the analyte dissolved in the same solvent (i.e., "standards") and performing similar light-absorbance measurements on unknown concentrations of analyte dissolved in the same solvent and on the standards. The most common procedure comprises plotting $A_\lambda$ versus concentration of analyte in the standards (i.e., a "standard curve") and then comparing the results obtained with the unknown concentrations of analyte to the standard curve. This procedure allows determination of the unknown concentrations of analyte from the "standard curve".

Vertical-beam photometers also measure light absorption in order to determine the unknown concentrations of analyte in samples. In vertical-beam, photometers, however, the light beam usually passes only through one wall of the sample-retaining device, through the sample, and then through the interface between the sample a surrounding gas atmosphere (which is usually air). The latter liquid-gas interface, the meniscus, is usually curved, the specific shape depending upon the interactions between the liquid sample and the gas and the side-walls of the sample retaining device. Depending upon the design of a particular vertical-beam photometer, the light beam may traverse the meniscus either before or after passing through the sample. In either case, the optical pathlength through the sample is not a constant value. Instead, the optical pathlength is related to the sample volume and the meniscus shape. The nature of the sample, the sample-retaining device surfaces, and gas each contributes to the shape of the meniscus, quantitatively affecting the optical pathlength through the sample. Thus, in vertical beam photometers, the value of l in Eq. 1 usually is unknown and is difficult to control reproducibly.

Vertical-beam photometry has become a popular technique despite the disadvantage of not having a fixed optical pathlength through the sample. This popularity stems from the fact that the optical characteristics of a large multiplicity of samples may be analyzed with a vertical-beam photometer in a small period of time. Typically, vertical-beam photometers monitor the optical characteristics of samples disposed in the wells of, for example, 96 well multi-assay plates. The optical characteristics, such as light absorption or light scattering, of the samples contained within each well of such multi-assay plates may be monitored, typically, in 10 seconds or less, and generally in one minute or less. Vertical-beam photometers also allow repetitive measurements of such a multiplicity of samples to be made typically with intervals of 10 seconds or less (and generally in one minute or less) between each of a series of measurements. In such a way the kinetic properties, such as the rate of change in absorbance, of a plurality of samples may be monitored in a very short time.

In vertical-beam photometry of the prior art, an approximated constant value of 1 is used for standards and unknowns. Concentrations of unknown analytes are determined, often with acceptable precision, by plotting "standard curves" using the approximated value of 1 and comparing the absorbance results obtained with unknown concentrations of analyte to the standard curve, as mentioned previously.

The fact that a value of C may not be calculated directly from Eq. 1, but instead must be determined from a standard curve constructed for each analytical measurement, severely hinders the ability of vertical-beam photometric techniques. The additional time and expense required for preparing such standard curves for each analysis is often an onerous disadvantage to vertical-beam photometry. Thus, convenient, accurate, and precise methods and apparatus for determining optical pathlength of samples in vertical-beam photometers would be of great utility.

Japanese Kokai Patent Application number Sho58[1983]-1679Y2 discloses that the unknown optical pathlength of vessels may be determined by dispensing a colored solution, with a known relationship between optical pathlength and color absorbance, into the vessels and determining the color absorbance of this solution. A similar method is taught in U.S. Pat. No. 5,298,978, issued Mar. 29, 1994.

Additionally Japanese Kokai Patent Application numbers Sho 60(1985]-183560 and Sho 61[1986]-82145 disclose methods of determining relative optical pathlength of aqueous samples within different reactor vessels (contained in a common reactor) by measuring the optical density of the samples at two different wavelengths in the near-infrared wavelength region from 900 to 2100 nanometers. With clear quartz reaction vessels, the reference teaches that $(A_{975}-A_{900})$, $(A_{1195}-A_{1070})$, or $(A_{1260}-A_{1070})$ may be used to determine the relative optical pathlength through aqueous samples. For reactors made of synthetic acryl resins, where the resin has interfering absorption bands, the prior art teaches that $(A_{970}-A_{1070})$ or $(A_{1280}-A_{1070})$ may be used to determine relative optical pathlength of the samples. Once relative optical pathlength is known for each of the vessels of the reactor, then optical density values of analyte (measured at a third wavelength) may be normalized for variation in optical pathlength to obtain the relative concentration of analyte in each reactor vessel. Employing vessels with known concentrations of analyte allows one to determine the absolute concentrations of analyte within other vessels.

There also exists need for methods and apparatus that may be utilized with samples that are dissolved in a variety of different solvents or in mixtures of different solvents. Because analytes are extremely diverse and may have diverse light-absorption properties, there exists no apparatus capable of determining concentration and optical pathlength of any analyte dissolved in various solvents or mixtures of solvents. Further complicating this situation is the extreme variability of concentrations of analytes from one sample to the next.

SUMMARY OF THE INVENTION

The instant invention provides a solution to the problem of undefined light absorbance pathlength in vertical-beam photometers. The invention provides methods and devices that are convenient to employ and that require minimal additional measurement apparatus. Thus, the cost associated with making such measurement is kept to a minimum.

The invention further provides methods and apparatus for determining optical pathlength and sample concentration that furnish accurate and reproducible results. The results, determined by using the invention in vertical-beam photometers, are essentially interchangeable and indistinguishable from those obtained in horizontal-beam photometry.

The invention also provides methods and apparatus for determining optical pathlengths between 1 millimeter and 1 centimeter in aqueous samples within vertical-beam photometers. The inventive methods and apparatus may be utilized with samples that are dissolved in a variety of different solvents or in mixtures of different solvents.

Thus, in one embodiment of the invention, optical pathlength is determined in vertical-beam photometers by analyzing an optical property of the sample solvent which is dependent upon optical pathlength but independent of all relevant concentrations of all analytes which may possibly be contained within a sample solvent.

In one aspect, the invention provides multi-channel photometric analysis devices for determining optical characteristics of analytes in sets of liquid-containing samples having unknown optical pathlengths. These devices comprise a. a first sample holder for holding the sets of liquid-containing samples in one or more substantially vertical optical channels;

b. a means for positioning the sets of samples in the optical channels;

c. a light source means, a wavelength selection means, and a light distribution means which cooperate to transmit light substantially vertically through the samples, wherein the light comprises a first calibration wavelength, a second calibration wavelength and an analyte-measuring wavelength, wherein the first and second calibration wavelengths are different and within the near infrared wavelength region of from 750 to 2500 nanometers and provide characteristic light signal values for each liquid sample, wherein there exists a predetermined relationship between the light signal values and the optical pathlength through the samples and wherein the analyte-measuring wavelength provides a characteristic analyte light signal value related to the concentration of analyte present in each sample;

d. a detector for determining measured light signal values from light transmitted through each sample at the first and second calibration wavelengths and the analyte-measuring wavelength;

e. a means for determining a measured relationship between the light signal values;

f. a means for determining from the measured relationship and the predetermined relationship a correction factor related to the optical pathlength through each sample;

g. a means for determining from the correction factor and the analyte light signal value, a ratio relating the analyte signal value to the optical pathlength in each of the samples.

The invention also encompasses vertical-beam photometric devices for measuring the rate of change in optical characteristics of samples contained in sample sites disposed on an assay plate, the device comprising:

a wavelength selection means for selecting a first wavelength band of light from a first wavelength range ad for selecting a second and a third wavelength bands of light from within a second wavelength range;

a sample-retaining means for retaining one, or more, samples, and a light-transmitting means for transmitting the light from the light source to the wavelength selection means and through the one, or more, sample;

a photodetector means for detecting the first, second and third bands of light transmitted through a selected sample, and for providing a first, a second and a third signal in respective relationship to the first, second and third bands of light so transmitted;

a means for determining the optical pathlength of the first band of light transmitted through the selected sample from the difference of the second and third signals; and a means for relating the first signal to the optical pathlength so determined so as to determine and automatically indicate optical parameters including either the absorbance or the fraction of incident light transmitted through the selected sample per unit optical pathlength of the selected sample and additionally a means for kinetic analysis of the signal of the photodetector means relating to the selected site so as to determine the rate of change of the optical parameters.

In another aspect, the invention provides multi-channel photometric analysis devices for determining optical characteristics of analytes in sets of liquid-containing samples having unknown optical pathlengths. In this aspect, the devices comprise:

a. a first sample holder for holding the sets of liquid-containing samples in one or more substantially vertical optical channels;

b. a means for positioning the sets of samples in the optical channels;

c. a light source means, a wavelength selection means, and a light distribution means which cooperate to transmit light substantially vertically through the samples, wherein the light comprises a first calibration wavelength and a second calibration wavelength, wherein the first and second calibration wavelengths are different and within the near infrared wavelength region of from 750 to 2500 nanometers and provide characteristic light signal values for each liquid sample, wherein there exists a predetermined relationship between the light signal values and the optical pathlength through the samples;

d. a detector for determining measured light signal values from light transmitted through each sample at the first and second calibration wavelengths;

e. a means for determining a measured relationship between the light signal values;

f. a means for determining from the measured relationship and the predetermined relationship a correction factor related to the optical pathlength through each sample;

g. a means for determining from the correction factor the optical pathlength in each of the samples.

In another aspect, the invention provides methods for determining the vertical optical pathlength through a liquid-containing sample comprising a. placing the liquid-containing sample in a sample holder which provides a substantially vertical light path through the sample, said vertical light path having an unknown optical pathlength through the sample;

b. transmitting light through the sample along the vertical light path, the light comprising a first calibration wavelength and a second calibration wavelength, the first calibration wavelength and the second calibration wavelength having different near infrared wavelengths within the range of from 750 nanometers to 2500 nanometers to provide two characteristic light signal values for the liquid with a predetermined relationship between the values and the vertical optical pathlength through the sample;

c. determining measured light signal values at the first calibration wavelength and at the second calibration wavelength;

d. determining from the measured light signal values, and the predetermined relationship, the vertical optical light path pathlength through the sample.

In yet another aspect, the invention provides methods for determining the amount of analyte in a liquid-containing sample comprising a. placing the liquid-containing sample in a sample holder which provides an unknown, substantially vertical, optical light path through the sample;

b. transmitting light through the sample along the vertical light path, the light comprising a first calibration wavelength, a second calibration wavelength, and an analyte-measuring wavelength, the first calibration wavelength and the second calibration wavelength having different near infrared wavelengths within the range of from 750 nanometers to 2500 nanometers to provide two characteristic light signal values for the liquid with a predetermined relationship between the values and the vertical optical pathlength through the sample;

and the analyte-measuring wavelength providing a characteristic analyte light signal value related to the quantity of analyte present in the vertical optical light path;

c. determining measured light signal values at the first calibration wavelength, the second calibration wavelength and at the analyte-measuring wavelength, said measured light signal values resulting from the passage of the light through the sample;

d. determining a measured relationship between the measured light signal values at the first and second calibration wavelengths;

e. determining from the measured relationship and the predetermined relationship a correction factor related to the pathlength of the vertical light path through the sample;

f. determining from the correction factor and the measured light signal value at the analyte-measuring wavelength the amount of analyte in the sample.

In a further aspect, the invention provides photometric analysis systems for determining the vertical optical pathlength through a liquid-containing sample comprising a. a sample holder into which the liquid-containing sample is placed and which provides a vertical light path through the sample where the vertical optical light path is unknown;

b. a light source which transmits light through the sample along the vertical light path, the light comprising a first calibration wavelength and a second calibration wavelength wherein
the first and second calibration wavelengths are different and within the near infrared wavelength region of from 750 to 2500 nanometers and provide two characteristic light signal values for the liquid with a predetermined relationship between the values and the vertical optical pathlength through the liquid;
c. a detector for determining measured light signal values at the first and second calibration wavelengths,
d. means for determining a measured relationship between the measured light signal values at the first and second calibration wavelengths; and
e. means for determining the vertical optical pathlength through the sample from the measured relationship.

In still another aspect, the invention provides a photometric analysis system for determining the amount of an analyte in a liquid-containing sample the system comprising
a. a sample holder into which the liquid-containing sample is placed and which provides a vertical light path through the sample where the vertical optical light path is unknown; and
b. a light source which transmits light through the sample along the vertical light path, the light comprising a first calibration wavelength, a second calibration wavelength and an analyte-measuring wavelength, wherein the first and second calibration wavelengths are different and are within the near infrared wavelength region of from 750 to 2500 nanometers and provide two characteristic light signal values for the liquid with a predetermined relationship between the signals and the vertical optical pathlength through the liquid, the analyte-measuring wavelength providing a characteristic analyte light signal value related to the quantity of analyte present in the vertical optical light path;
c. detector for determining measured light signal values at the first and second calibration wavelengths and the analyte-measuring wavelength;
d. means for determining a measured relationship between the light signal values measured at the first and second calibration wavelengths;
e. means for determining from the measured relationship and the predetermined relationship a correction factor related to the vertical optical pathlength through the sample; and
f. means for determining the amount of the analyte in the sample from the correction factor and the measured light signal value at the analyte-measuring wavelength.

DESCRIPTIONS OF THE PREFERRED EMBODIMENTS

Figure 1:
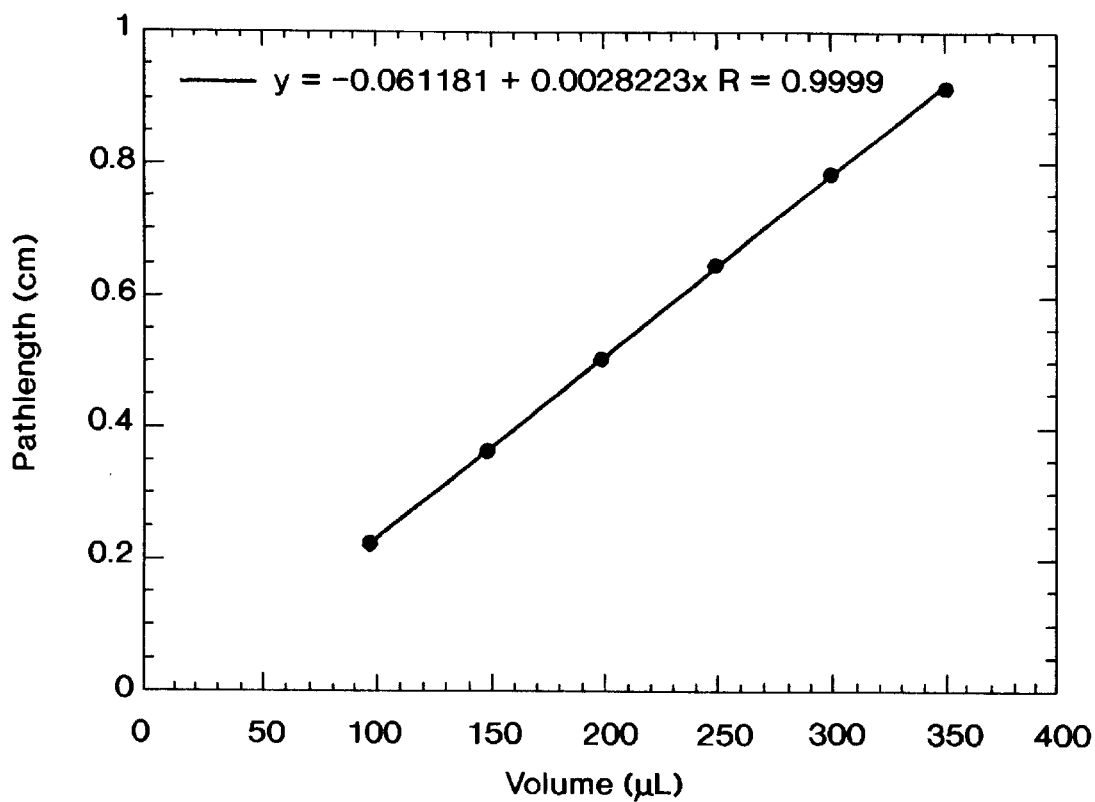
FIG. 1 is a graph showing calibration of pathlength versus volume in a NUNC 96-well microplate.

The disclosed invention comprises photometric methods and devices for determining Light Absorption Pathlength of liquid samples containing analytes dissolved or suspended in a solvent. The methods and devices rely on determining a relationship between the light absorption properties of the solvent and the optical pathlength of liquid samples containing the solvent. This relationship is used to establish the Light Absorption Pathlength for samples having an unknown Light Absorption Pathlength, but having a similar solvent composition. Such samples, for example, may be contained within a plurality of wells disposed in a multiassay plate, such as a 96-well microplate, in a vertical-beam photometer. Such vertical-beam photometers are able to measure absorbance of analytes within such samples at predetermined wavelengths of light. According to the invention such vertical-beam photometers may automatically determine and indicate, to an analyst carrying out a chemical measurement, the concentration of an analyte. The automatic determination is made, according to Equation (1), from (a) the absorbance of the analyte in the sample, (b) the Light Absorption Pathlength determined according to the invention, and (c) a predetermined "extinction coefficient of the analyte. In such a way novel photometer devices automatically determine and indicate the concentration of analytes in such multi-assay plates directly without employing a standard curve.

Generally, the methods and devices of the invention rely on separately determining light absorption by the solvent and, at a different wavelength, light absorption by the analyte. Devices for carrying out the methods particularly advantageously include vertical-beam absorbance photometers with sample retaining means for containing samples disposed within the wells of multi-assay plates, wherein the photometer is able to monitor light absorption of each sample at multiple wavelength bands, including bands in the visible or UV-visible region of the spectrum, as well as bands in the near-infrared region of the electromagnetic spectrum.

The invention, however, is not limited to photometers that measure light absorption solely. Rather the invention is useful generally in vertical-beam photometers that measure optical characteristics in samples where the optical pathlength through a sample is not known but where it is desirable to know such optical pathlength. The invention will find general utility in vertical-beam photometers that, additionally, measure other optical properties of liquid samples, including, but not limited to fluorescence, phosphorescence, chemiluminescence, or light scattering. Thus the invention is useful for chemical measurement by vertical-beam photometers where the measurement is made by either light absorptivity, fluorometry, phosphorometry, chemiluminometry, turbidimetry (where the loss of light from the optical pathlength is measured as optical density) and nephelometry (where the light scattered off the optical axis is measured). When utilizing the invention to measure optical properties of samples other than light absorbance, the invention will monitor light absorbance, of the solvent in the sample, in combination with optical properties of the sample other than light absorbance.

As used herein, A indicates an absorbance value measured according to Eq. 1 and a subscripted value following A indicates the center of the bandpass spectrum of light (given in nanometers) that is used to make the light-absorbance measurement. For example, $(A_{1770}-A_{1310})$ is the mathematical difference between absorbance measurements, made on the same sample with the same optical pathlength, with 1770 nanometer and 1310 nanometer center bandpass incident light respectively. In certain situations the fraction of incident light transmitted ($I/I_O$) may be employed rather than the amount of light absorbance ($\log I_O/I$) after accounting for the mathematical relationship between these two parameters.

The solvents suitable for use in the invention and apparatus of the invention may be any solvent although those absorbing light in the near-infrared region are preferred. Particularly preferred solvents are those having low ultraviolet and visible absorbance spectra. Such solvents are those typically having low electronic transition probabilities at energy levels corresponding to light of 180 to 750 nanometer wavelength. For electronic transition probabilities of various solvents, see "High Purity Solvent Guide," James T. Przybytek, ed., 1992, Burdick & Jackson Laboratories, Inc., Muskegon, Mich.

As used herein, the near-infrared portion of the electromagnetic spectrum is that portion extending from about 750 to 2500 nanometers (ie., from about 0.750–2.5 microns wavelength or, in wavenumbers, about 13,300–4000 cm$^{-1}$). Liquid water absorbs light with values of $\epsilon_\lambda \cdot C$ between 0.01 and 60 cm$^{-1}$ at absorption bands located within the near infrared region. At room temperature, the values of $\epsilon_\lambda \cdot C$ for pure water is about 0.18 cm$^{-1}$ near 970 nanometers and is about 0.58 cm$^{-1}$ near 1200 nanometers wavelength. These values may be found in Luck, Berichte der Bunsengesellschaft 67: 186–189, 1963; and Thomas et al., *The Journal of Physical Chemistry* 69:3722–2726, 1965.

The light absorption pathlength customarily employed in vertical-beam photometry is between 1 millimeter and 1 centimeter.

According to Eq. 1, the values of $A\lambda$ at wavelengths of about 970 nanometers and about 1200 nanometers are 0.018 or 0.058, respectively, for a 1 millimeter light absorption pathlength and 0.18 or 0.58, respectively, for a pathlength of 1 centimeter in pure water at room temperature. These values are well within the range of 0.01 to 4.0 absorbance units which is generally desirable for precise optical density measurements in vertical-beam photometers.

It has been unexpectedly discovered that near-infrared analysis of water at selected wavelengths is sufficiently robust to give an inaccuracy of less than 5% variation from the true pathlength value in vertical-beam photometry. This discovery is surprising since: (1) absorption of light by molecules in the near-infrared region (NIR) of the electromagnetic spectrum is due to overtones or combinations of overtones originating from fundamental absorption bands in the mid-infrared region extending from 4000 to 600 cm$^{-1}$; (2) absorbance in the mid-infrared region is due to intra-molecular bond stretching and bending vibrational motions and is highly dependent upon the extent of hydrogen bonding in aqueous solutions; and (3) physical parameters such as temperature or ionic strength, for example, influence the absorption coefficient and wavelength of maximum absorption. In addition, analytes present in water may potentially influence hydrogen bonding within the solvent, thus changing the light absorption properties of the water solvent. These problems are discussed in the *Handbook of Near-Infrared Analysis*, Donald A. Burns, Emil W. Ciurczak, eds., Marcel Dekker, Inc. 1992. See also, G. L. Kemeny and D. L. Wetzel, "Moisture: Study of a Lively Near-Infrared Diffuse Reflectance Spectrum, "Paper 117, FACSS 13$^{th}$ Annual Meeting, Sept. 28–Oct. 3, 1986, St. Louis Mo.; and G. L. Kemeny and D. L. Wetzel, "Differences in the Spectrum of Water, "AACC Annual Meeting, Nov. 1–6, 1987, Nashville, Tenn. Furthermore, samples analyzed by vertical-beam photometry customarily have a curved meniscus and no single unique pathlength exists for all rays of light passing through the sample.

The methods and apparatus of the invention may be used to determine various light absorption pathlengths within vertical-beam photometers containing samples, preferably light absorption pathlengths between about 1 millimeter and 1 centimeter. Further, the invention may be used with a variety of solvents and analytes. Disclosed herein are four embodiments suitable for determining light absorption pathlengths. These methods and apparatus each utilize measurement of absorbance of the sample solvent in the near-infrared region of the electromagnetic spectrum (NIR)

The first embodiment is especially well suited for use in determining optical pathlength in purely aqueous solvents within a moderate temperature range. This embodiment may be used at temperatures from about room temperature to the temperature of the human body (i.e., from about 20 to 40° C.).

The second embodiment may be used to determine light absorption pathlength for samples having an analyte in aqueous solvents over a broader range of temperatures, i.e., from about 0 to 100° C.

The third embodiment is suitable for determining light absorption pathlength in mixtures of aqueous and non-aqueous solvents.

Finally, the fourth embodiment is preferred for use with nonaqueous solvents having values of $\epsilon_\lambda \cdot C$ of from about 0.05 to 5 cm$^{-1}$ for absorption bands located within the near infrared to infrared regions of the electromagnetic spectrum from about 800 to 6000 nanometers.

Vertical-beam photometers suitable for carrying out the invention will have the following:
1. a light source, such as tungsten halogen, xenon flash lamp, mercury arc lamp, or the like;
2. a wavelength selection means capable of selecting bands of light in the ultraviolet-visible region of the electromagnetic spectrum from between 180 to 750 nanometers. (These ultraviolet-visible bands will normally be used for analysis of concentration of analytes in samples comprised of at least one analyte dissolved in a solvent);

3. a wavelength selection means capable of selecting bands of light in the infrared region of the electromagnetic spectrum greater than 750 nanometers;
4. a light-distribution means, such as optical lenses and mirrors for directing light, or a system of fiber optics for directing the light;
5. a sample-retaining means for retaining samples disposed on a multi-assay plate, such as the NUNC 96-well microplate; and
6. a light detection means, such as photo-diodes, photo-conduction cells, a photo-multiplier, photo-Darlington cells, a diode-array, or the like capable of detecting both the bands of the light in the ultraviolet visible region and the bands of light in the infrared region.
7. a means for determining the optical pathlength of the samples, as described above.

Suitable wavelength selection means for both the ultraviolet-visible region and the infrared region of the electromagnetic spectrum include optical filters of colored glass, or the like, interference filters, or monochromators for dispersing the light and selecting a band of light. With either filters or a monochrometer the bands of light desirably will be narrow in the range of 1 to 25 nanometers bandwidth. Preferably the bands will be even narrower, but not so narrow as to unduly limit the amount of light provided, generally in the 5–10 nanometer range. Usually the wavelength selection means capable of selecting bands of light in the infrared region will need to select bands of light only in the near-infrared region of the electromagnetic spectrum from 750 nanometers to 2500 nanometers wavelength. Alternatively, a laser, such as a helium-neon, argon ion, carbon dioxide, or solid state laser, e.g. a GaAlAs laser, could be used to fulfill both the requirement for a light source and a wavelength selection means. When more than one band of wavelengths is desired, two, or more, lasers or light-emitting diodes may be combined as the light source and the desired wavelength range may be supplied by turning on the light source emitting the desired wavelength band of light. Such lasers have the advantage of having high light intensity at extremely narrow bandwidth. Alternatively, light-emitting diodes (LEDs) may be used to supply light of the desired wavelength range. A variety of LEDs may be used selectively to provide the desired wavelength bands of light when switched from on to off. Alternatively, the LEDs or laser sources of light may be used in conjunction with a white light source, together with optical filters or a monochrometer. In this way, the wavelength range and intensity of the white light source may be extended at a desired wavelength.

A vertical-beam photometer suitable for monitoring the absorbance of liquid samples in the ultraviolet-visible and the near-infrared portions of the electromagnetic spectrum when fitted with the appropriate interference filters, is described in U.S. Pat. Nos. 4,968,148 and 5,112,134. A vertical-beam photometer disclosed in pending U.S. patent application Ser. No. 08/228,436 also would be suitable when fitted with a monochrometer capable of providing bands of light in the near-infrared portion of the electromagnetic spectrum. Such a monochomater is Part No. 36-0504 available from Optometrics Inc., Ayer, Mass. All documents, e.g., patents and journal articles, cited above or below are hereby incorporated by reference in their entirety.

All documents, e.g., patents and journal articles, cited above or below are hereby incorporated by reference in their entirety.

A particularly preferred instrument and software for carrying out the present invention is the SPECTRAmax®PLUS microplate spectrophotometer. In the following examples a SPECTRAmax®PLUS microplate spectrophotometer was used and is available commercially from Molecular Devices Corporation.

Figure 11:
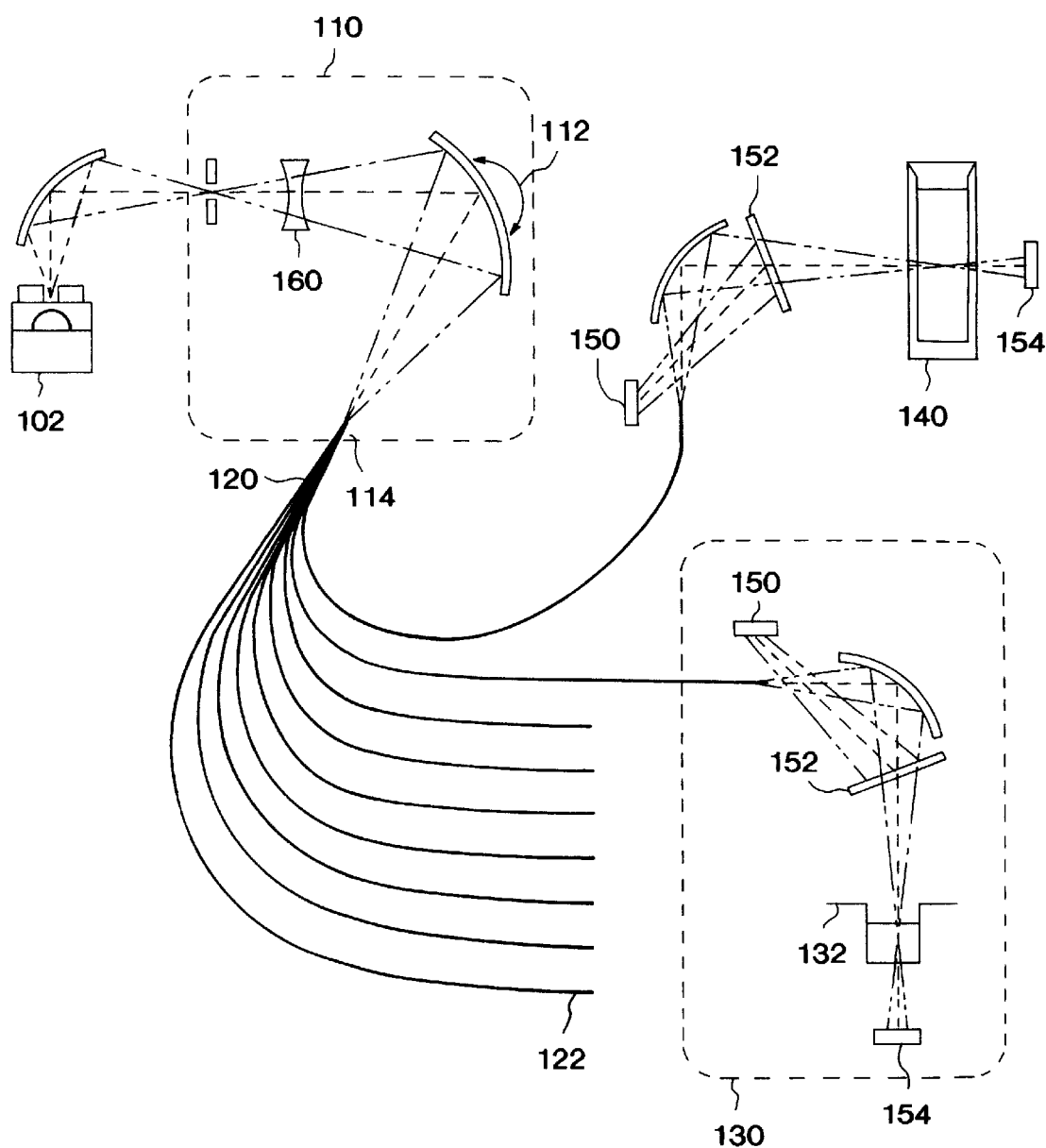
FIG. 11 is a schematic representation of a more preferred embodiment of the present invention.

A schematic representation of the optical design of an apparatus of the invention, as embodied in a SPECTRAmax®PLUS microplate spectrophotometer is shown in FIG. 11. Such a microplate spectrophotometer has a xenon flash lamp as a light source 102. Light produced by source 102 is dispersed by a monochrometer 110, having a diffraction grating 112, onto a monochrometer exit slit 114. The selected light exiting through the exit slit 114 is resolved into wavelength bands of 2 nm (full width at half-height) which are selectable in 1 nm increments between 190 and 1000 nanometers by moving the angle of the grating 112 with respect to the exit slit 114.

As shown in FIG. 11, nine optical fibers 120 are arranged linearly at the exit slit to collect the selected light into 9 optical fiber channels 122. Eight of the fiber channels 122 are used to direct the selected light to 8 individual channels of a vertical-beam photometer chamber 130 which is adapted to hold multi-assay plates 132. The plates are retained by a multi-assay plate housing 131 (not shown). The housing accommodates multi-assay plates 135 such as standardized 96-well microplates with sample wells in a 8×12 rectangular array, or alternatively, multi-well, linear, sample strips, such as standardized 8-well strips. The optics 133 (not shown) of the vertical-beam photometer chamber are adapted to allow the light to pass substantially vertically through fluid samples in the multi-assay plate 135 so as to pass through a gas/liquid interface in each sample (i.e. passing through a meniscus) as is customary for vertical-beam photometry.

The remaining optical fiber is used to carry the selected light to a cuvette housing 134 which is adapted to hold a rectangular cuvette 140 or a rounded tube (e.g. a standard 1 cm pathlength optical cuvette or test tube). The optics of the cuvette housing are adapted to allow the light to pass through fluid samples in the cuvette without passing through a gas/liquid interface (i.e. without passing through a meniscus) as is customary for horizontal-beam photometry.

A first silicon photodetector 150 related to each optical fiber channel is positioned to collect light diverted by a beam-splitter 152 positioned to reflect light before it has passed through the space where the fluid samples are placed (i.e., the sample position). A second silicon photodetector 154 related to each optical fiber channel is positioned to collect the light after it has passed through the sample position. The ratio of photocurrents from the two photodetectors in each channel is used to compute the optical density of (or % transmission of light passing through) the fluid samples (relative to a reference such as air only in the sample position). This arrangement of photodetectors is utilized both in cuvette housing 134 and the vertical-beam photometer chamber 130.

Cuvettes 140 are placed manually in cuvette housing 134 and fluid samples are placed one-at-a-time in a cuvette 140 for optical density measurements. In contrast, multiple samples may be placed in the wells of multi-assay plates 132. Light from each of the 8 parallel optical fiber channels passes simultaneously through up to 8 wells of a multi-assay plate allowing 8 simultaneous optical density measurements in 8 different wells of the plate. A motorized plate carrier repositions the multi-assay plate so that subsequent groups of 8 wells are interrogated by the 8 optical channels. In sequence, this process is repeated until all samples have been interrogated, 8 at a time. For example, when a standard 96-well multi-assay plate with samples arranged in a 8 rows×12 columns in a rectangular array is used, the plate carrier repositions the multi-assay plate 12 times sequentially, so as to interrogate simultaneously the 8 samples in each of the 12 columns.

For determination of optical pathlength of aqueous samples, near-infrared interference filters 160, mounted on a motor-driven filter wheel 162 (not shown) in monochrometer 110, are individually selected and placed in the optical path of the microplate spectrophotometer. The interference filters are ½ inch diameter and have a 10 nanometer bandpass (nominally centered within 5 nanometers of 1000 nanometers and near 900 nanometers, respectively). Light from the flash lamp passes through the filters and reflects off the optical grating and into the exit slit 114 having the optical fibers. Maximal light throughput is achieved when the optical grating 112 is placed at its "zero order" angle where light originating from the flash lamp is reflected into the monochrometer exit slit 114 without diffraction. The optical fibers 120 direct the light to the individual channels of a vertical-beam photometer chamber 130 and to the cuvette housing 134 as described above.

Alternatively, the grating 112 of monochrometer 110 may be positioned so that bands of light centered within 5 nanometers of 1000 nanometer center wavelength or 900 nanometer wavelength are diffracted onto exit slit 114 having optical fibers 122. In this alternative embodiment, optical filters 160 and filter wheel 162 are not needed. Also in this alternative embodiment, the nominally 900 nanometer and 1000 nanometer bands of light directed into optical fibers 122 will have similar bandpass as other UV, visible and near infrared light diffracted by grating 112 onto monochrometer exit slit 114 (in this example 2 nanometers).

In still another alternative embodiment, the width of the monochrometer slit may be adjusted, either manually or automatically by an electrical apparatus such as a motor or solenoid, to provide a selected bandpass of light. In this way a bandpass value may be selected for each center wavelength of light. Generally bandpass values will be between 1 nanometer and 10 nanometers. More generally bandpass values can be between 0.25 and 25 nanometers.

Optionally solvent (e.g. water) contained in a reference cuvette of known optical pathlength is used to calibrate the instrumental determination of solvent pathlength. Cuvette 140 in cuvette housing 134 may be used for this purpose. For example, light from the flash lamp is passed through the 1000 nm interference filter and absorption by the solvent in the reference cuvette is measured. Customarily, the combined effects of light reflectance and absorption are measured by comparison of the light intensity transmitted through the solvent and the light intensity transmitted through air (with neither the sample nor the sample retaining device, i.e. the cuvette, present). Next light from the flash lamp is passed through the 900 nm interference filter and absorption by the solvent in the reference cuvette again is measured. Again, the combined effects of both light reflectance and absorption are measured by comparison of the light intensity transmitted through the solvent and the light intensity transmitted through air (with neither the sample nor the sample retaining device, i.e., the cuvette, present). Loss of transmitted light due to reflection and absorption by the cuvette is approximately the same at the two wavelengths, thus the difference in (calculated absorbance) values obtained in the two measurements gives the differential absorbance of substantially only the solvent at the two wavelengths of light. The difference in absorbance values observed divided by the optical pathlength of the reference cuvette employed is the calibration value for this specific pair of filters. An experimental value of 0.1433 absorbance units/cm optical pathlength was found for a specific 1000 nm/900 nm filter pair where water, between 15° C. and 37° C., is used as the solvent. This value is used in the examples described below. See Example 11.

One skilled in the art will recognize that modifications may be made in the present invention without deviating from the spirit or scope of the invention. The invention is illustrated further by the following examples which are not to be construed as limiting the invention or scope of the specific procedures described herein.

Experimental Measurements a) Instrumentation:

A Theromax™ microplate reader, commercially available from Molecular Devices Corporation, Menlo Park Calif., USA, is used to make all vertical-beam photometry measurements. Nominally 1000, 900, and 970 nanometer (center bandpass wavelength) inference optical filters may be obtained from Andover Corporation, Salem, N.H. Also, in this instance, the nominally 900 nanometer filter (Cat. No. 900FS10-25) is centered at 902.6 nanometers with 11.5 nanometer bandpass (bandwidth at half maximal transmittance). Also in this instance, the nominally 970 nanometer filter (Cat. No. 970FS10-25) is centered at 970.0 nanometers and has 8.5 nanometer bandwidth at half maximal transmittance. Other optical filters were obtained as catalog items from Molecular Devices Corporation. Horizontal-beam photometric measurements, made for comparative purposes, are made in a Hewlett-Packard Model 8451A diode array spectrophotometer equipped with a 1 cm light path cuvette.

b) Reagents:

The following reagents may be obtained form Aldrich Chemical Co., Milwaukee, Wis.: Acid Orange 8 (Cat. No. 21,453-1), Acid Orange 74 (Cat. No. 20,181-2), Azure B (Cat. No. 86,105-7), Direct Yellow 62 (Cat. No. 20,206-1), Naphthal Green B (Cat. No. 11,991-1). Bromocresol Purple was obtained from Sigma Chemical Co. (Cat. No. B-4263). The spectra of these compounds in the ultraviolet and visible regions of the electromagnetic spectrum is given in, *The Sigma-Aldrich Handbook of Stains, Dyes and Indicators*, by Floyd J. Green, 1990 Aldrich Chemical Co., Inc., Milwaukee, Wis. Durkee Yellow Food Color may be obtained from Durkee Famous Foods SCM Corporation, Westlake, Ohio. Schilling Blue Food Color was obtained from McCormick & Co., Inc., P.O. Box 208, Hunt Valley, Md. Obtainable from Sigma Chemical Co. is PIPES (Piperazine-N,N'-bis[2-ethar sulfonic acid]), sodium salt, Cat. No. P-6757.

c) Multi-assay plates:

For vertical-beam photometry, samples are contained within wells of a 96-well microplate multi-assay plate. The microplates are Nunclon® Delta 96-well, flat-bottom plates which may be obtained from VWR Scientific, Brisbane, Calif.

d) Experimental conditions:

Measurements reported in the below example were made at room temperatures between 20 and 25 degrees centigrade.

EXAMPLE 1

In this example a vertical-beam photometer was also used as a horizontal-beam photometer in the near infrared at wavelengths greater than 800 nm. For these horizontal-beam measurements, a 1.00 cm pathlength quartz cuvette is filled with water and capped with a Teflon® stopper which is taped to the cuvette. The capped cuvette was placed horizontally in a vertical-beam photometer so that a selected band of incident light is passed through one clear (transparent) wall of the cuvette, next through the water sample, and finally through the opposite clear (transparent) wall of the cuvette before being measured by the photodetector of the photometer. The results of such measurements are equivalent to measurements made by horizontal-beam photometry. The band of incident light is first selected by passing through either the nominally 900 nanometer center-band or the 970 nanometer center-band interference filter (each of which have approximately a 10 nanometer bandpass). The resulting photometric values were used as L Values of $I_O$ for each optical filter were obtained with neither the water sample nor the cuvette in the incident light path (air blank). Absorbance values are calculated by the photometer at each pre-selected wavelength by using Eq. 1. The difference in absorbance values of the 1.00 cm optical pathlength cuvette filled with water measured with the nominally 970 nanometer center-band filter used to provide incident light and the 900 nanometer center-band filter used to provide incident light (i.e. $A_{970}-A_{900}$) was found to be 0.180. Horizontal beam photometry at wavelengths less than 800 nm was performed with the Hewlett-Packard Model 8451 A spectrophotometer.

Next, similar measurements of $(A_{970}-A_{900})$ were performed on six different samples containing chromophoric analytes. Prior to measurement, the analytes were dissolved in the deionized water at concentrations sufficient to yield samples having absorbance values of between 1.0 and 3.0 absorbance units at their respective maximal light absorption wavelengths in the visible spectral region when placed in the same 1 cm optical pathlength cuvette. The analytes are Acid Orange 8, Acid Orange 74, Azure B, Direct Yellow 62, Durkee Yellow Food Color. The values of $A_{970}-A_{900}$ obtained experimentally for each of the analytes in aqueous solution range from 0.180 to 0.183. A similar measurement for another analyte comprising Bromocresol Purple in a solvent mixture of 12 mM PIPES (Piperazine-N,N -bis[2-ethanesulfonic acid]) and 38 mM Sodium Phosphate Buffer (1.0 parts 0.05 M PIPES: 3:14 parts 0.05 M Sodium Phosphate Buffer by volume, final pH=5.8), similarly was found to be 0.183. From Eq. 1, and employing two absorbance measurements, $A_{\lambda 1}$, and $A_{\lambda 2}$, at two different wavelengths, $(\lambda_1)$ and $(\lambda_2)$, we have $(A_{\lambda 1}-A_{\lambda 2})=(\epsilon_{\lambda 2}-\epsilon_{\lambda 1})\cdot l\cdot C$. The value of $(\epsilon_{\lambda 2}-\epsilon_{\lambda 1})\cdot C$ for these aqueous analytes at room temperature, is about 0.182 $cm^{-1}$. Based upon this result, values of $(\epsilon_{970}-\epsilon_{900})\cdot C$ within this range, predictably might be employed generally to calculate light absorption pathlength from measured values of $(A_{970}-A_{900})$ for a variety of aqueous samples (referred to as Sample $A_{970}-A_{900}$) at room temperature. According to this prediction obtained from a small number of experimental samples, light absorption pathlength may be determined for aqueous samples at temperatures ranging from about 15 to 40° C., preferably about 23° C., according to Eq. 2 with less than about 5% error as follows:

$$\text{Light Absorption Pathlength} = \frac{\text{Sample}(A_{970} - A_{900})}{0.182 \text{ cm}^{-1}} \quad (2)$$

Absorbance of samples per unit pathlength may be found by measuring the absorbance, $A_x$, of samples at a preselected wavelength, x, preferably near the absorbance maximum of the analyte. The resulting values are referred to as Sample $A_x$. Light Absorbance per unit Pathlength in aqueous samples is calculated using equation 3, as follows:

$$\text{Light Absorption per Unit Pathlength} = \frac{\text{Sample } A_x \ (0.182 \text{ cm}^{-1})}{\text{Sample } A_{970} - A_{900}} \quad (3)$$

From these results and the temperature data provided in Berichte der Bunsengesellschaft, supra, even greater precision may be obtained by a) measuring the temperature of the sample, or alternatively of the sample compartment enclosing the aqueous sample, and b) adjusting the 0.182 $cm^{-1}$ value [i.e., $(\epsilon_{970}-\epsilon_{900})\cdot C$] in the denominator of the right side of Eq. 2 and the numerator of Eq. 3 for the estimated temperature of the sample. For example, for aqueous samples at 2° C., the adjusted 0.182 $cm^{-1}$ value would be about 0.157 $cm^{-1}$, for 10° C. about 0.168 $cm^{-1}$, for 20° C. about 0.180 $cm^{-1}$, for 30° C. about 0.190 $cm^{-1}$, for 40° C. about 0.200 $cm^{-1}$, for 50 °C. about 0.210 $cm^{-1}$, for 60° C. about 0.220 $cm^{-1}$, for 70° C. about 0.230 $cm^{-1}$, for 80° C. about 0.240 $cm^{-1}$ and for 90° C. about 0.250 $cm^{-1}$. Intermediate values of $(\epsilon_{970}-\epsilon_{900})\cdot C$ for intermediate temperatures may be obtained by interpolation.

In this example, the cuvette, filled with aqueous sample and sealed at the top, was placed horizontally in the light beam of the vertical-beam photometer without the use of any fixed retaining means. These horizontal-beam photometric measurements made at the individual 970 and 900 nanometer wavelengths varied by as much as ±0.050 absorbance units from measurement to measurement. The differential $A_{970}-A_{900}$ values, however, varied by no more than ±0.002 absorbance units. Thus, the $A_{970}-A_{900}$ value is relatively independent of the angle of the incident test light with respect to the sample cuvette in horizontal-beam photometry. Differential measurements, such as the $A_{970}-A_{900}$ value, therefore function to eliminate errors due to variation of cuvette angle with respect to the beam of test light in horizontal-beam photometry. Alternatively a fixed sample-retaining means would also help to reduce such errors.

Next the same sample solutions were dispensed into the wells of a 96-well microplate at sample volumes of 350, 300, 250, 200, 150, or 100 µl per well. Each sample composition and volume combination was tested in 8 replicate wells of the microplate. Absorbance values for each well within the microplate, with incident light passing substantially vertically through the wells, were measured in the vertical-beam photometer at the same center-band wavelengths employed for the respective samples in the horizontal-beam spectrophotometer measurements. "Solvent blank," absorbance values of the pure water solvent were also measured in the vertical-beam vs. an "air blank" at each measurement wavelength. The appropriate "solvent blank" at each center-band wavelength of incident light is subtracted from the experimental absorbance measurements, which employed "air blank" values of $I_O$ according to Eq. 1 above. These individual, "solvent blank" corrected absorbance values are determined for each analyte near its wavelength of maximal absorbance in each well of the microplate. Also, the optical pathlength (i.e. the light absorption pathlength) is calculated from sample $A_{970}-A_{900}$ data obtained from each well in the microplate according to Eq. 2 above. The individual, "solvent blank"-corrected absorbance values determined for each analyte near its wavelength of maximal absorbance are then divided by the optical pathlength for each well of the microplate. These values are termed specific absorbance values. The specific absorbance values of each analyte (i.e., the absorbance per unit pathlength, reported in units of $cm^{-1}$) are shown in Table I, below.

TABLE I

Optical Density/Cm Pathlength Measured In
A Vertical-Beam Photometer vs. A Spectrophotometer

| Chromophore (wavelength) | Absorbance per Centimeter Pathlength [A/cm (cm$^{-1}$)] Microplate Volume | | | | | | A/cm Microplate 150–350 µl Mean ± S.D. (cm$^{-1}$)(CV in %) | A/cm Horizontal-Beam Spectrophotometer (cm$^{-1}$) | Microplate vs. Spectrophotometer Difference (cm$^{-1}$);(% diff.) |
|---|---|---|---|---|---|---|---|---|---|
| | 350 µl | 300 µl | 250 µl | 200 µl | 150 µl | 100 µl | | | |
| Acid orange 8 (490 nm) | 2.37 | 2.33 | 2.32 | 2.33 | 2.34 | 2.37 | 2.34 ± 0.019 CV = 0.00% | 2.28 | 0.06 (2.5%) |
| Acid Orange 74 (480 nm) | 1.59 | 1.59 | 1.59 | 1.59 | 1.59 | 1.61 | 1.59 ± 0.000 CV = 0.00% | 1.54 | 0.05 (3.2%) |
| Azune B (650 nm) | 1.43 | 1.44 | 1.44 | 1.46 | 1.45 | 1.47 | 1.44 ± 0.000 CV = 0.76% | 1.46 | 0.02 (1.0%) |
| Blue Food Color (630 nm) | 1.67 | 1.67 | 1.67 | 1.67 | 1.66 | 1.68 | 1.67 ± 0.004 CV = 0.24% | 1.66 | 0.01 (0.6%) |
| Bromcresol Purple (420 nm) | 1.15 | 1.15 | 1.17 | 1.16 | 1.16 | 1.18 | 1.155 ± 0.008 CV = 0.52% | 1.10 | 0.05 (4.8%) |
| Bromoresol Purple (590 nm) | 0.996 | 0.992 | 1.008 | 0.999 | 1.001 | 1.019 | 0.999 ± 0.006 CV = 0.60% | 0.955 | 0.04 (4.6%) |
| Direct Yellow 62 (340 nm) | 1.70 | 1.70 | 1.70 | 1.70 | 1.73 | 1.76 | 1.71 ± 0.013 CV = 0.76% | 1.70 | 0.01 (0.4%) |
| Yellow Food Color (420 nm) | 2.67 | 2.62 | 2.59 | 2.59 | 2.59 | 2.61 | 2.61 ± 0.019 CV = 0.73% | 2.62 | 0.01 (0.3%) |

As shown in Table I, the coefficient of variation (CV) for the measurement of specific absorbance values, made at the five greatest sample volumes, for each of the seven different analytes, and made at eight different wavelenghts, was less than 1%. Further, even lowest volume (100 µl) samples yielded acceptable specific absorbance results. The CV of the specific absorbance measurements for the 100 µl samples, however, slightly exceeded 1%. The reason for this increase in CV at the lowest volume (100 µl ) is that optimal precision in vertical-beam photometers requires an optical density of 0.100, or greater. As shown in FIG. 1, in a typical 96-well microplate, a 100 µl volume only gives about 0.2 cm optical (light absorption) pathlength. Employing the relationship shown in equation 2 above, we see that a 100 µl aqueous volume in these microplates will produce only about 0.036 absorbance units in $A_{970}$–$A_{900}$ which is substantially less than the 0.100 required for optimal precision.

Because there is diminished precision with such small sample volumes (between 10 and 100 µl) for example, in preferred embodiments, precision of better than 1% may be obtained in determination of light absorption pathlength by averaging multiple measurements of $A_{970}$–$A_{900}$.

Absorbance values measured in a horizontal-beam spectrophotometer with identical sample solutions in a 1 cm light path cuvette are similar to those obtained with the vertical-beam photometer, after correcting for the determined optical (light absorption) pathlength.

Particularly preferred results are obtained when the concentration of solvent is relatively unchanged by the analyte. For example, the concentration of water in one (1) molar sodium chloride aqueous solution, at 0° C., is about 55.6, substantially the same (within 1%) as for pure water at the same temperature. Thus, any optical property of water that is dependent upon the light absorption pathlength within the water, as well as the water concentration, may be used to monitor the optical pathlength within aqueous samples containing analytes, provided that the optical property is otherwise unaffected by such analytes.

It is preferred, in most aqueous samples to maintain a high concentration of the water solvent relative to the concentration of the dissolved analytes.

It is further preferred that absorbance measurements of the solvent not be made exactly at the wavelength of maximal absorbance of the solvent. Instead, absorbance measurements are preferably made at a center-band wavelength selected to be between a local maximum and a local temperature isosbestic or "pseudo-isosbestic" point in absorbance of the solvent in the NIR. Such temperature "pseudo-isosbestic" wavelengths exist for light absorbance by solvents such as water. At such temperature "pseudo-isosbestic" wavelengths absorbance by the solvent is nearly independent of temperature.

In general, the wavelength where two absorbing chemical species in equilibrium have identical absorptive optical properties is called an isosbestic point. Such isosbestic points are often taken as evidence for the existence of at least two inter-convertible absorbing forms of a species and which forms have overlapping absorption spectra. For example, the absorption spectra of simple pH indicator dyes, (e.g. Phenol Red) show isosbestic points as a function of pH. Phenol red, for example, has an isosbestic point at 495 nanometers, where the protonated form absorbs optimally close to 420 nanometers, and unprotonated form of the dye absorbs maximally at 560 nanometers wavelength. The equilibrium between the protonated and unprotonated forms of the dye shifts as a function of temperature due to a non-zero ionization enthalpy of the dye. Thus, at this (wavelength) isosbestic point of Phenol Red will also be observed a temperature isosbestic point because although the relative ratio of unprotonated and protonated forms of the dye are temperature dependent, the light absorptive properties of both forms of the dye are substantially unaffected by temperature variation.

In contrast, when two inter-convertible absorbing forms of a species with overlapping spectra exist but the measured optical property of at least one of the individual chemical species is affected by a variable, the "perfect" isosbestic is destroyed. For example spectral narrowing or broadening of an individual chemical species with temperature variation will result in such a phenomenon. If the variation from a perfect isosbestic is slight, a "pseudo-isosbestic" is said to exist. Such pseudo-isosbestic points are, in fact, observed in the near-infrared absorptive properties of water, as a function of both temperature and ionic strength variation. At both isosbestic and "pseudo-isosbestic" wavelengths the absorbance values of solvents are nearly unaffected by temperature or hydrogen-bonding influences. Water, for example, has multiple "pseudo-isosbestic" wavelengths, with respect to temperature variations, which occur between about 980–1010 nanometers, again near 1080–1120 nanometers, again near 1180–1200 nanometers, again near 1280–1320 nanometers, again near 1440–1460 nanometers, and again near 1750–1800 nanometers. Therefore, when the optical pathlength for aqueous samples is determined from NIR absorbance measurements in these spectral regions, the variation in the results due to temperature and hydrogen-bonding variations from sample-to-sample, is minimized. It is further preferred that the following absorbance differences for water, $(A_{1000}-A_{900})$, $(A_{1190}-A_{1100})$, $(A_{1440}-A_{1310})$, or $(A_{1770}-A_{1310})$ will be measured in order to determine the optical pathlength of aqueous samples. It is preferred that the center bandpass wavelength be within 10 nanometers of the pseudo-isosbestic or isosbestic wavelengths given above. It may be sufficient, however, for the center bandpass wavelength in most cases to be within 20 nanometers.

The $(A_{1000}-A_{900})$ absorbance differences are preferred NIR wavelengths for measuring absorbance with the silicon photodetectors present in the "Theromax" microplate reader employed for these measurements. Since silicon photodetectors do not provide reasonable detectivity at wavelengths substantially greater than 1100 nanometers, the $(A_{1000}-A_{900})$ absorbance difference is selected as the absorbance difference of choice to monitor the absorbance of water to obtain suitable absorbance values at the preselected wavelength with samples as small as 150 $\mu l$ and to ensure that the CV of the measurements are less than 1%. Alternatively, greater precision and less sensitivity to temperature and sample variations can be obtained by providing vertical-beam photometers with light detectors having good detectivity in the NIR region longer than 1100 nanometers wavelength. Suitable detectors include, for example, thermal-type detectors, such as thermocouples, thermistor or pneumatic devices. Alternatively, NIR semiconductor photodetectors, such as InGaAs, PbS, InAs, or Ge detectors, could be used. With these infrared photo-detectors, any of the above other disclosed "pseudo-isosbestic pairs," $(A_{1185}-A_{1100})$, $(A_{1444}-A_{1310})$, or $(A_{1770}-A_{1310})$, could be used directly to monitor the light absorbance pathlength of water. With such alternative photodetectors, the $(A_{1185}-A_{1100})$ pair is most optimal because the absorbance of water at 1185 nanometers is about 0.545 per cm of pathlength, which is very nearly optimal for maximum signal-to-noise ratios in vertical-beam photometers employing light-absorbance pathlengths of from 0.2 cm to 1.0 cm.

A suitable wavelength bandpass (wavelength bandwidth at half-maximal intensity) for these measurements is about 10 nanometers. Bandpass values of from 0.5 to 15 nanometers are acceptable, narrower bandpass values restrict the intensity of available light unduly. Wider bandpass values result in undue loss in amplitude of differential absorbance measurements.

The isosbestic center bandpass wavelengths given in this example are preferred. In practice, a range of center bandpass wavelengths, is acceptable for practice of the invention. Generally, for the 900 nm wavelength the acceptable center bandpass range is quite broad, from about 750 nm to about 925 nanometers. Generally, for the 1000 nm isosbestic wavelength, the acceptable center bandpass range is from about 980 nm to about 1020 nanometers. For the 1100 nm isosbestic wavelength, the acceptable center bandpass range is from about 980 nm to about 1150 nanometers. For the 1190 isosbestic wavelength, the acceptable center bandpass range is from about 1175 nam to about 1210 nanometers. For the 1310 nm isosbestic wavelength, the acceptable center bandpass range is from about 1175 nm to about 1350 nanometers. For the 1440 nm isosbestic wavelength, the acceptable center bandpass range is from about 1430 mn to about 1465 nanometers. For the 1700 nm isosbestic wavelength, the acceptable center bandpass range is from about 1720 nm to about 1820 nanometers. Further, the differences in absorbances at the given pairs of isosbestic wavelengths are preferred. It should be recognized, however, that any of the isosbestic wavelengths may be paired with any other isosbestic wavelength in order to determine a difference in absorbance that is related to the pathlength of the solvent (and which difference will be approximately independent of temperature).

EXAMPLE 2

The method described in this example allows measurements of optical pathlength with mixtures of aqueous and nonaqueous solvents. It also provides for correction when substances, other than water (that may absorb at the NIR wavelengths selected to monitor optical pathlength in vertical-beam photometry) are present in the solvent. In this example the differential NIR absorbance $(A_{970}-A_{900})$ is used to monitor pathlength in aqueous samples. Alternatively, the "pseudo-isosbestic pairs," described above provide superior results under certain conditions. For example, the (Alooo-Agoo) pair will provide superior results with silicon photodetectors when the temperature is highly variable. The $(A_{1185}A_{1100})$ pair will provide superior results when the temperature is variable and when a vertical-beam photometer is used which employs photodetectors sensitive to light at wavelengths of 1100 and 1185 nanometers in the NIR because larger absorbance values may be obtained with smaller light absorbance pathlengths. This method is as follows:

1. Load the solvent employed (to dissolve the analyte) into a cuvette of known optical pathlength, for example, a 1 cm optical pathlength cuvette. This pathlength is known as the Solvent Pathlength. Place the cuvette in a photometer and measure $(A_{970}-A_{1000})$. This parameter is referred to as Solvent $(A_{970}-A_{900})$ (The cuvette may be stoppered and placed on its side in the incident light path of vertical-beam photometers in order to accomplish this step.)

2. Repeat part 1 in the same known optical pathlength cuvette, now with the analyte of interest in the solvent. The resulting parameter is referred to as Reference $(A_{970}-A_{900}.)$ Also, measure, approximately, the absorbance, $A_x$, of the analyte at the wavelength which will be used for subsequent measurements of analyte concentration. This parameter is referred to as Reference $A_x$. Preferably, the concentration of the analyte should be adjusted so that the absorbance of the analyte is a value between 1.0 and 2.0.)

3. Measure the values of $A_x$ in samples with the vertical-beam photometer as is customary. These parameters are referred to as Sample $A_x$. Also, measure $(A_{970}-A_{900})$ values of the samples with the vertical-beam photometer. The later parameter is referred to as Sample $(A_{970}-A_{900}.)$ The light absorption pathlength in each of the samples is determined using equation 4 as follows:

Light Absorption Pathlength = (4)

$$\frac{Sample(A_{970} - A_{900}) - \left\{\frac{Sample\ A_\chi}{Reference\ A_\chi}\right. }{\left. [Reference(A_{970} - A_{900}) - Solvent(A_{970} - A_{900})]\right\}}{\dfrac{Solvent(A_{970} - A_{900})}{Solvent\ Pathlength}}$$

Light Absorbance per unit Pathlength for the samples is determined from equation 5 as:

Shown in Table II are the measurements of absorbance of Napthal Green B in aqueous solvent samples determined according to the method set forth in this example above. For comparison purposes the results are determined according to Eq. (3) and according to Eq. (5). The Light Absorbance per unit Pathlength measurements made (as described in Example 1) according to Eq. (3) in the vertical-beam photometer (microplate reader) were greater than the results obtained in the spectrophotometer by 101% (i.e. more than 2-fold greater). Eq. 5, however, provides results from the vertical-beam measurements with the vertical-beam photometer that are substantially identical to those from the horizontal-beam spectrophotometer.

TABLE II

Light Absorbance/Cm Pathlength of an Interfering Analyte Determined with and without correction for the Optical Interference of Napthal Green B

| Naphthal Green B | Absorbance per Centimeter Pathlength ie. A/cm (cm$^{-1}$) Microplate Volume | | | | | | A/cm Microplate 150–350 µl Mean ± S.D. | A/cm Horizontal-Beam Spectrophotometer | Microplate vs. Spectrophometer difference |
|---|---|---|---|---|---|---|---|---|---|
| (725 nm) | 350 µl | 300 µl | 250 µl | 200 µl | 150 µl | 100 µl | (cm$^{-1}$)(CV in %) | (cm$^{-1}$) | (cm$^{-1}$)(% diff.) |
| Uncorrected A/cm (Eq. 3) | 2.40 | 2.39 | 2.40 | 2.41 | 2.44 | 2.51 | 2.41 ± 0.019 CV = 0.08% | 1.2 | 1.21 (+101%) |
| Corrected A/cm (Eq. 5) | 1.21 | 1.20 | 1.21 | 1.21 | 1.22 | 1.23 | 1.21 ± 0.07 CV = 0.06% | 1.20 | 0.01 (+0.8%) |

Light Absorbance per unit Pathlength = (5)

$$\frac{Sample\ A_\chi \cdot Solvent(A_{970} - A_{900})}{Solvent\ Pathlength} \bigg/ \left\{ Sample(A_{970} - A_{900}) - \left\{\frac{Sample\ A_\chi}{Reference\ A_\chi}\right. \right. $$
$$\left. \left. [Reference(A_{970} - A_{900}) - Solvent(A_{970} - A_{900})]\right\}\right\}$$

Preferably, the means for determining optical pathlength and automatically determining and indicating light absorbance per unit pathlength (i.e., specific absorbance) are included in a vertical-beam photometric device capable of monitoring the optical density of samples contained in a multi-assay plate at a minimum of three (3) different centerband wavelengths of incident light. The device preferably will include means for determining and indicating if the analyte presents significant interference with a simple, uncorrected, determination of Optical Pathlength. An Interference Parameter is determined from equation 6 as follows:

Interference Parameter = (6)

$$\frac{Sample\ A_\chi [Reference\ (A_{970} - A_{900}) - Solvent(A_{970} - A_{900})]}{Reference\ A_\chi \cdot Sample(A_{970} - A_{900})}$$

Significant interference is deemed to be absent when the Interference Parameter given by Eq. 6 is between 0.05 and −0.05, for example. Thus, the interference of the analyte creates less than a 5% error in determination of Optical Pathlength. The device preferably will include automatic means for determining and indicating when any of the parameters Sample $A_\chi$, Sample $(A_{970}-A_{900})$, Reference $A_\chi$, Reference $(A_{970}-A_{900})$ or Solvent $(A_{970}A_{900})$ are less than 0.05 and, thus, too low to provide an accurate estimation of interference or specific absorbance.

The procedure described in this example also allows Light Absorption Pathlength and Light Absorbance per unit Pathlength to be determined for mixtures of aqueous and nonaqueous solvents. Such mixture may include, for example, water, methanol, ethanol, propanol, acetone, acetonitrile, pyridine, glycerol, tetrahydrofuran, di-and trichlorobenzenes, or derivatives thereof, and organic esters such as methyl- or ethyl-acetate. Any mixture of a nonaqueous, i.e., organic, and aqueous solvent may be employed. Multi-assay plates that are resistant to such solvents include multi-assay plates made of glass, quartz, or other polymeric material resistant to nonaqueous solvents. Suitable quartz 8- or 96-well multi-assay plates are available from Hellena Laboratories, Beaumont Tex. and from Molecular Devices Corporation, Menlo, Park, Calif. (Part Nos. R1077 or R1076).

It should be readily apparent that absorbance of the aqueous solvent may be measured at any of the isosbestic center bandpass wavelength pairs described in example #1 above. For example, $(A_{1000}-A_{900})$, or any other suitable isosbestic center bandpass wavelength, could be used advantageously to eliminate temperature effects in the determination of Light Absorption Pathlength, Light Absorbance per unit Pathlength, or Interference Parameter. The acceptable center bandpass ranges are the same as described in example #1 above.

EXAMPLE 3

The method described in this example may be employed with any solvent, including solvents substantially free of water. For this method the absorbance spectrum of the desired solvent is determined in the NIR. Two wavelengths are then selected, a first wavelength near an absorbance maximum, denoted as $A_{max}$, of the solvent; and a second wavelength near an absorbance minimum denoted as $A_{min}$, of the solvent. The difference in absorbance of samples at the first and second wavelengths, ($A_{max}$–$A_{min}$,) should preferably be selected to be between 0.050 and 5.0. It is particularly preferred that the value of ($A_{max}$–$A_{max}$) be selected to be between 0.1 and 1.0. The method is conducted as follows:

1A. Load the solvent employed to dissolve the analyte into a cuvette of known (pre-determined) optical pathlength, for example, a 1 cm optical path cuvette. This optical pathlength is known as the Solvent Pathlength. Place the cuvette in a photometer and measure ($A_{max}$–$A_{min}$.) This parameter is referred to as Solvent ($A_{max}$–$A_{min}$.) (The cuvette may be stoppered and placed on its side in the light path of a vertical-beam photometer in order to make this measurement.)

2A. Repeat step 1A, as described above in the same known optical pathlength cuvette with the analyte of interest now in the solvent. This parameter is referred to as Reference ($A_{max}$–$A_{min}$.) Also measure, approximately, the absorbance, $A_x$, of the analyte at the wavelength which will be used for subsequent measurements of analyte concentration. This parameter is referred to as Reference $A_x$. Preferably, absorbance of the analyte is between about 0.5 and 2.0)

3A. Measure the values of $A_x$ in samples with the vertical-beam photometer. These parameters are referred to as Sample $A_x$. Also measure ($A_{max}$–$A_{min}$) values of the samples with the vertical-beam photometer. The later parameter is referred to as Sample ($A_{max}$–$A_{min}$).

The light absorption pathlength in each of the samples is determined from equation 7 as follows:

$$\textit{Light Absorption Pathlength} = \frac{\textit{Sample}(A_{\max} - A_{\min}) - \left\{\frac{\textit{Sample } A_x}{\textit{Reference } A_x}[\textit{Reference}(A_{\max} - A_{\min}) - \textit{Solvent}(A_{\max} - A_{\min})]\right\}}{\frac{\textit{Solvent}(A_{\max} - A_{\min})}{\textit{Solvent Pathlength}}} \quad (7)$$

Light Absorbance per unit Optical Pathlength for samples is determined using equation 8:

$$\textit{Light Absorbance per unit Pathlength} = \frac{\frac{\textit{Sample } A_\chi \cdot \textit{Solvent}(A_{\max} - A_{\min})}{\textit{Solvent Pathlength}}}{\textit{Sample}(A_{\max} - A_{\min}) - \left\{\frac{\textit{Sample } A_\chi}{\textit{Reference } A_\chi}[\textit{Reference}(A_{\max} - A_{\min}) - \textit{Solvent}(A_{\max} - A_{\min})]\right\}} \quad (8)$$

In general, this method provides for determining the absorbance of an analyte per unit light absorption pathlength (or fraction of light transmitted by an analyte per unit light absorption pathlength) wherein the analyte is suspended or dissolved in a liquid solvent such that a relationship between light absorption of the analyte and the light absorption pathlength of the analyte are unknown. This method also provides for determination of the concentration of the analyte according to Equation (1) from (a) the absorbance of an analyte in the sample, (b) the light absorption pathlength of sample, and (c) a predetermined extinction coefficient of the analyte. If the analyte interferes with determination of the light absorption pathlength, or if solvents other than water are present, the relationship between absorbance of the solvent and absorption pathlength (or the amount of interference) may be quantitated, thus allowing a correct light absorption pathlength to be determined.

In general, a first, a second and a third light signal resulting from, respectively, a first, second, and third predetermined wavelength of light transmitted through substantially identical optical pathlength within a sample and wherein a difference between the first and the second light signals (e.g. $A_{970}$–$A_{910}$) is related to the light absorption pathlength and the third light signal (e.g. $A_{490}$ where Acid Orange 8 is the analyte) is related to both the light absorption pathlength and the concentration of the analyte. The light absorption properties of the sample solvent may be determined, independently of the analyte by measuring a forth and fifth light signal (e.g. $A_{970}$ and $A_{910}$) resulting from, respectively, the first and the second wavelength of light transmitted through a predetermined optical pathlength (e.g. 1 cm) of the solvent which is employed as a first reference liquid. Comparison of the difference in the first and second light signals (e.g. $A_{970}$–$A_{910}$ of the sample) and the forth and fifth light signals (e.g. $A_{970}$–$A_{910}$ of the solvent) allows the known light absorption pathlength of the solvent to be compared directly to the unknown light absorption pathlength of the sample.

Provided that the sample does not interfere with determination of the light absorption pathlength, the concentration of the analyte may be determined form absorbance of the sample at the third wavelength (e.g. $A_{490}$, where Acid Orange 8 is the analyte) or the fraction of light transmitted at the third wavelength per unit light absorption pathlength, from the predetermined light pathlength, the third light signal, the difference in the first and second light signal and the difference in the fourth and fifth light signals.

When the sample interferes with determination of the light absorption pathlength, the concentration of the analyte may be determined by measuring a relationship between absorbance of the analyte at the third wavelength and its (interfering) absorbance at the first and second predetermined wavelengths. Thus, a second reference liquid, containing the analyte, is prepared and used to measure a sixth and a seventh light signal resulting from, respectively, the first and second predetermined wavelengths of light transmitted through a predetermined light pathlength of the second reference liquid (e.g. $A_{970}$–$A_{910}$ of the second reference solution). The second reference liquid also is used to measure an eight light signal at the third predetermined wavelength (e.g. $A_{490}$, where Acid Orange 8 is the analyte) in a predetermined pathlength. The effect of sample interference may be eliminated substantially from determination of light absorption pathlength according to the example as shown in equation 7. Similarly the effect of sample interference may be eliminated substantially from determination of light absorption per unit pathlength according to the example shown in Equation 8. Thus, the light absorption pathlength, light absorption per unit pathlength, fraction of light transmitted per unit pathlength, or concentration of analyte (according to Equation 1) may be determined from the predetermined optical pathlength and from the first, second, third, fourth, fifth, sixth, seventh and eighth light signals.

Preferably, the means for determining Light Absorption Pathlength and for determining and indicating Light Absorbance per unit Optical Pathlength automatically are included in a vertical-beam photometric device capable of monitoring the optical density of samples contained in a multi-assay plate at a minimum of three (3) different center-band wavelengths of light. The device preferably will include means for determining and automatically indicating if the analyte presents significant interference with a simple, uncorrected, determination of Light Absorption Pathlength. An Interference Parameter, is determined using equation 9 as follows:

$$\text{Interference parameter} = \frac{\text{Sample } A_x[\text{Reference}(A_{\max} - A_{\min}) - \text{Solvent}(A_{\max} - A_{\min})]}{\text{Reference } A_x \cdot \text{Sample}(A_{\max} - A_{\min})} \quad (9)$$

There are a variety of uses for the methods and devices of the invention. For example, the volume of samples collected from a fraction-collector in the wells of a multi-assay plate may be desired. In such a determination, the relationship between Sample Volume and Light Absorption Pathlength would be first determined according to any one of the methods provided above. This procedure is carried out in the following example.

EXAMPLE 4

The data established in Example 1 above were used to determine the relationship between Light Absorption Pathlength and Sample Volume in the Nunclon® Delta 96-well, flat-bottom multi-assay plates utilized in that Example. Measurements of $A_{970}-A_{900}$ were performed on six different chromophoric analytes, Acid Orange 8, Acid Orange 74, Azure B, Direct Yellow 62, Durkee Yellow Food Color, and Schilling Blue Food Color, in aqueous solvent. The sample solutions were dispensed into the wells of the multi-assay plate at either 350, 300, 250, 200, 150, or 100 µl sample volume per well. Each sample and volume combination was tested in 8 replicate wells of the microplate.

The values of Sample ($A_{970}-A_{970}$) obtained experimentally were used to determine Light Absorption (i.e., optical) Pathlength for each well according to Eq. 2. FIG. 1 shows the volume of sample pipetted into each well vs. the mean Light Absorption Pathlength so determined and averaged for all of a given volume. The result shows that, for the 96-well NUNC microplate, the linear relationship described by equation 10 is observed:

Light Absorption Pathlength=[(2.82 cm/ml) (Sample Volume)]−0.0612 cm  (10)

The correlation coefficient for this linear relationship was 0.9999. The inverse of this relationship is described by equation 11 for a 96-well NUNC microplate as follows:

$$\text{Sample Volume} = \frac{(\text{Light Absorption Pathlength} + 0.0612 \text{ cm}) \text{ml}}{2.82 \text{ cm}} \quad (11)$$

Equation 11 may be used to determine the approximate volume contained within the wells of such a multi-assay plate upon determining the Light Absorption Pathlength of the samples. Further, with suitable calibration, this procedure may be used to determine the volume contained in the wells of any type of assay plate. The wells of the microassay plates may be of various geometric shape, including flat-bottom, round-bottom (U-bottom), V-bottom, or any other shape. Any geometry or shape of wells in the multi-assay plate may be employed as long as the relationship between sample volume from the Light Absorption Pathlength is substantially reproducible (generally within 5%). The relationship need not be linear, as is shown above for NUNC microplates which have cylindrical (flat-bottom) wells. It is only necessary to determine this relationship utilizing a multiplicity of known volumes of samples, and then determining Light Absorption Pathlength for the samples of known volume. This relationship may be used subsequently, together with Light Absorption Pathlength determinations in individual wells of multi-assay plates to estimate the liquid volume present within such plates.

EXAMPLE 5

This example demonstrates utility of the invention in the field of chromatography. Chromatography is used, generally, to separate analyte components in a sample mixture. Generally in chromatography, there exists a mobile phase and a stationary phase. The sample is applied in the mobile phase at the input of a means of retaining the stationary phase, e.g. a tubular column with a mesh support at the output of the column. As the mobile phase passes over the stationary phase the analytes bind to the stationary phase for more, or less time, depending on their affinity for the stationary phase, and therefore appear at different times at the output of the column. Separation of analytes in a sample is thereby accomplished when, "fractions" of the mobile phase, at the output of the column, are collected over time. In chromatography, generally, one wishes to analyze the amount, or concentration, of analyte present in each fraction collected. Furthermore, for reproducible chromatographic systems, carried out under constant conditions, (e.g. constant temperature, constant stationary phase, constant mobile phase, constant flow rate, constant column volume, etc.,) the same analyte will usually appear at the same "elution volume," (i.e. after the same volume of mobile phase has passed through the column). For such reproducible systems, one generally wishes to have a plot of the relative concentration of each analyte as a function of elution volume. The below example discloses utility of the instant invention in obtaining such "chromatograms" simply and conveniently while employing a vertical-beam photometer.

Certain, commercially-available fraction collectors may be employed conveniently to collect fractions directly in the wells of 96-well microplates such as the NUNC microplate employed above. For example, one such fraction collector is manufactured by the Gilson Corporation, Middleton, Wis. Generally, such fraction collectors collect fractions for a given time interval, or alternatively, such fraction collectors may count the droplets at the output of the chromatographic column and each fraction may contain a certain predetermined number of droplets. One problem is that each fraction contains a different, and unknown volume whenever the flow rate is not maintained constant for the time interval method, and whenever the surface tension of the mobile phase is not maintained constant for the drop-counting method. Therefore, analysis of the fractions collected in a multi-assay plate by vertical-beam photometry will give absorbance values for each fraction that will be influenced both by the concentration of analyte present and by the volume of analyte present in the sample. The two variables, concentration and volume, thereby are confounded and a method for determining the two variables separately is needed. One method of the prior art is to manually measure the volume of each fraction, to withdraw a known volume from each well to transfer the withdrawn volume into a second multi-assay plate and to measure the optical density of each well in the second multi-assay plate. This prior art procedure suffers from the disadvantage that it is tedious, cumbersome, and prone to errors made during the volume-measuring and transferring steps. The method described below provides for a less tedious and cumbersome procedure and may be automated so as substantially to avoid errors.

In the present example, immunoglobulin (IgG) protein molecules were covalently-labeled with a fluorescent, fluorescein moiety. The reagent for labeling the protein was an NHS ester of fluorescein as provided in the Immuno-Ligand Assay Labeling Kit, Cat. No. R9002, Molecular Devices Corp., Menlo Park, Calif. The IgG was reacted with the labeling reagent at 40:1 molar ratio of reagent to protein in pH 7.0 phosphate-buffered saline (PBS) according to the instructions provided by the commercial supplier of the reagent. The reaction product, in 0.3 ml volume, was applied to a PD-10 column containing G-25 Sephadex® gel filtration media (Pharmacia, Uppsula Sweden) as the solid phase. The column was eluted with 0.1 ml aliquots of PBS applied successively to the top of the column. Each fraction was collected, into a separate well of a NUNC 96-well microplate, from the time of application of each 0.1 ml aliquot of PBS until the column ceased to flow. After the flow ceased, the output of the column was switched to a new well of the microplate and the next aliquot of 0.1 ml of PBS was applied and the next fraction collected, etc.

Figure 2:
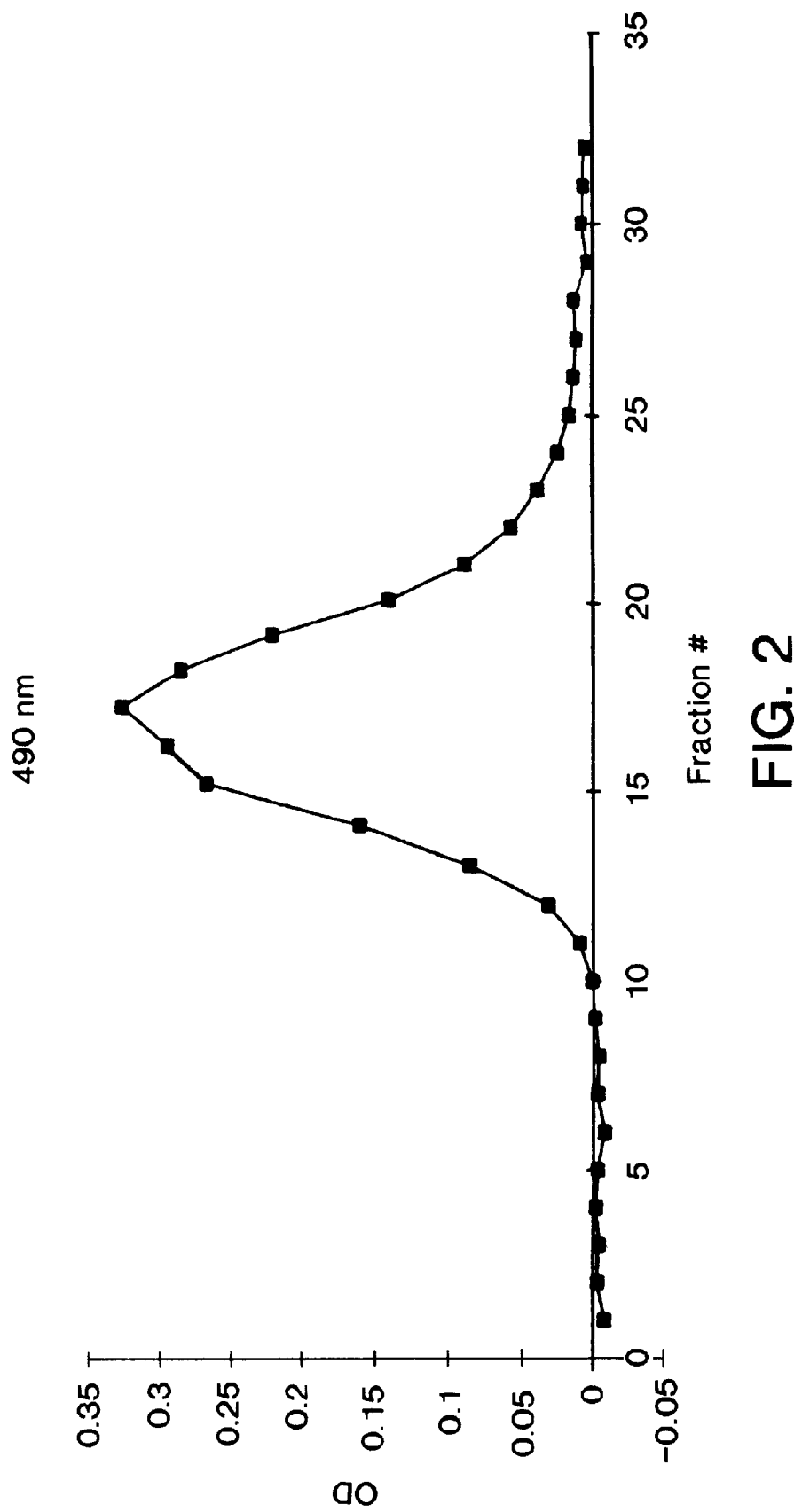
FIG. 2 is a graph showing the results of measuring the optical density of fractions at 490 nm in a vertical-beam photometer.
Figure 3:
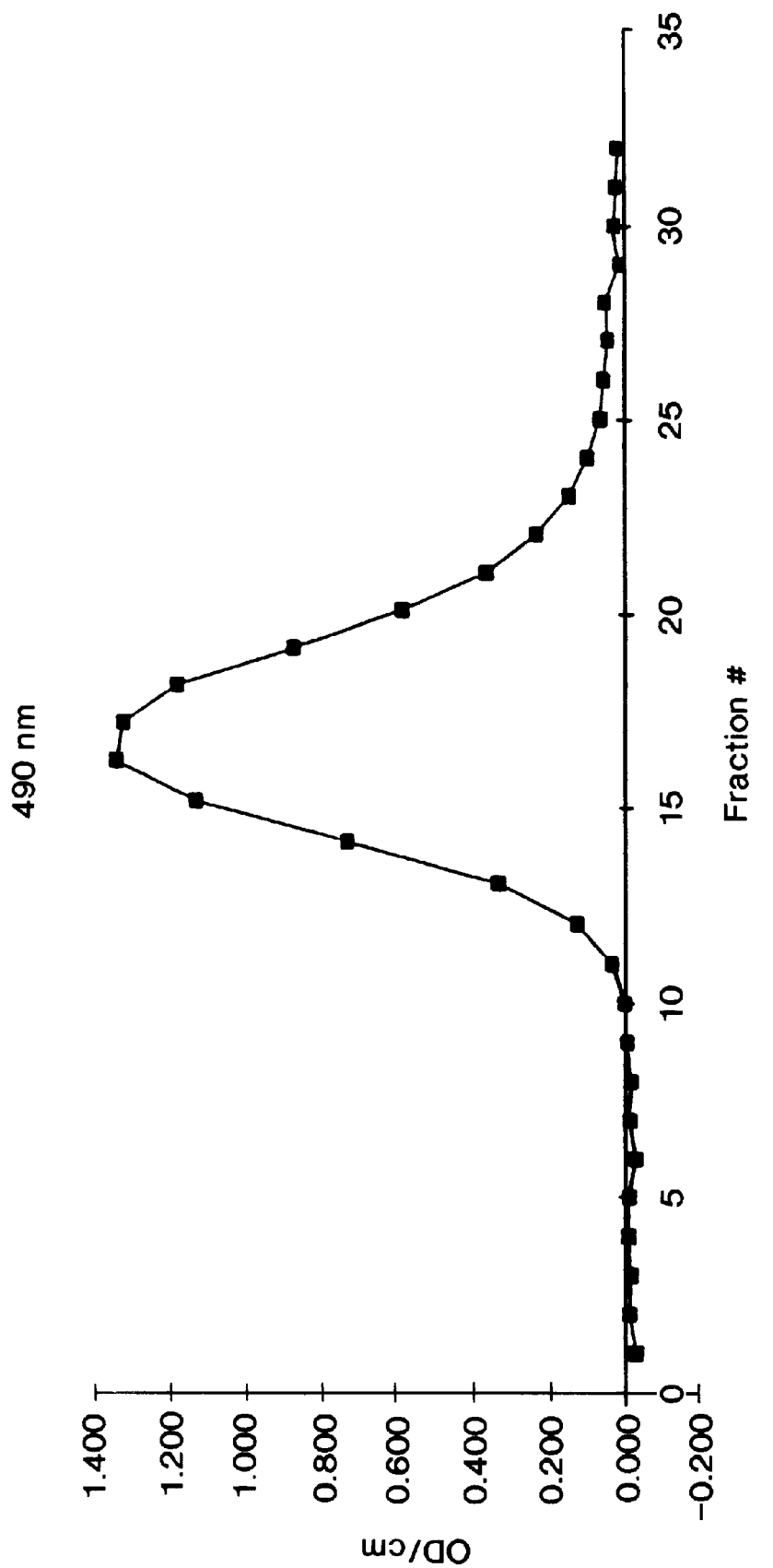
FIG. 3 is a graph of the results of measuring the optical density of fractions at 490 nm in a vertical-beam photometer where the results have been corrected for the light absorption pathlength of each fraction so as to indicate optical density per unit (cm) optical pathlength of each fraction.

FIG. 2 shows the results of measuring the optical density of each fraction at 490 nanometer wavelength in a Spectramax 250 vertical-beam photometer (Molecular Devices Corporation, Menlo Park, Calif.). The first fraction was collected for analysis after discarding the first 1.5 ml of PBS collected from the column. As seen in FIG. 2, a maximum in $OD_{490}$ was observed at fraction 17 where the labeled protein eluted from the column, as determined by similarly measuring the optical density of the fractions at 280 nanometers, which also shows a maximum in absorption of fraction 17. Unreacted labeling reagent eluted from the column in subsequent fractions are not shown in the figures. The shape of the curve shown in FIG. 2 is somewhat irregular. This irregularity, apparently, is not due to irregular variation in the concentration of IgG but is due to irregularity in the optical pathlength of the individual fractions. Shown in FIG. 3 are the same data corrected for light absorption pathlength of each fraction. The shape of the elution pattern of the labeled protein appears much more regular in FIG. 3, where the $OD_{490}$ per cm pathlength (i.e., the specific $OD_{490}$) is plotted for each fraction compared to FIG. 2 where only the $OD_{490}$ is shown. The light absorption pathlength in each fraction was determined by monitoring the difference in absorbance at 970 and 900 nanometer center-band pass wavelengths of near-infrared light in the Theromax vertical-beam photometer and calculated according to equation 2.

Figure 4:
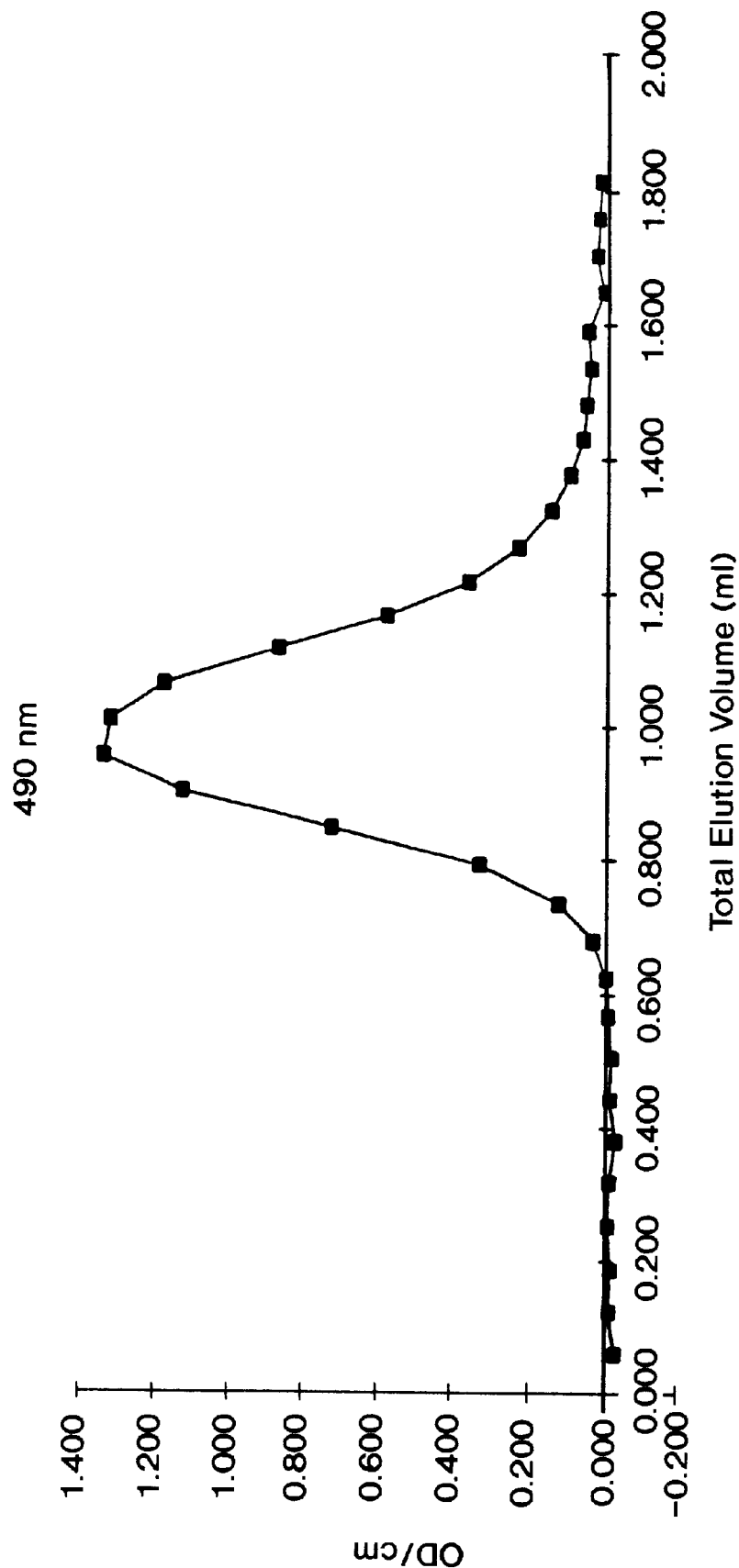
FIG. 4 is a plot of total elution volume versus the optical density measured at 490 nm for the combined volumes of the wells in a NUNC 96-well microplate.

Further shown in FIG. 4 are the same data shown in FIG. 3, except that the cumulative volume (after the first 1.5 ml. eluted from the column) appears on the ordinate of the plot. The cumulative volumes were determined by employing the relationship of Equation 11, established for PBS in NUNC 96-well flat bottom microplates, to determine the volume of each fraction from the measured optical density difference at 970 and 900 nanometer center-band pass wavelength and the light absorption pathlength values calculated from these data and equation 2. The volumes of each subsequent fraction then were summed to determine the cumulative elution volume. Each $OD_{490}$ per cm optical pathlength point is plotted at the mean cumulative elution volume of an individual fraction.

EXAMPLE 6

Elimination of error in Determination of Optical Pathlength due to Variation in Solvent Temperature Data have been gathered for a series of aqueous biological buffer solutions, which now permit further optimization of wavelength selection in the near infrared portion of the electromagnetic spectrum ("NIR") for use in determining optical pathlength of samples dissolved in such aqueous buffers. The NIR portion of the electromagnetic spectrum extends from 750 to 2500 nanometers wavelength. In this NIR range, light detection means may be detectors made of indium-gallium arsenide; gallium arsenide, germanium, cadmium sulfide, lead sulfide, or the like. Preferably the measurement wavelengths will be between 750 and 1100 nanometers so that silicon photodetectors may be used as a light detection means. Silicon photodiodes generally are useful in the range of 180 nanometers to 100 nanometers wavelength.

The following reagents were prepared: One-tenth molar (0.1 M) N-[2-Hydroxyethyl] piperazine-N'-[2-ethanesulfonic acid] (HEPES) was prepared from HEPES (1.0M) obtained from Sigma Chemical Co., St. Louis Mo. (Cat. No. H0887), by dilution into de-ionized water. One-tenth molar (0.1 M) Tris(hydroxymethyl) aminomethane (TRIS), pH 7.12, was prepared from 1.0 M TRIS obtained from BioRad Laboratories, Hercules, Calif. (Cat. No. 161-0719) by dilution into de-ionized water. The 0.1 M sodium phosphate was prepared by mixing 61 ml of 1.0 M sodium phosphate monobasic, (Cat. No. S369-1) and 39 ml of sodium phosphate dibasic, (Cat. No. S374-500) each from Fisher Scientific Pittsburgh, Pa. and diluting into de-ionized water. Threshold Assay Buffer was prepared by dilution of Concentrated (10x) Threshold Assay Buffer obtained from Molecular Devices Corporation, Sunnyvale, Calif. (Cat. No. R3030-1) and diluted to 1x(pH 57.02) in de-ionized water. Dulbecco's phosphate buffered saline solution, pH7.3 (PBS), was obtained from Irvine Scientific (Cat. No. 9236). One-tenth molar (0.1M) 2[N-Morpholino]ethanesulfonic acid (MES) buffer, pH 6.14, was prepared from MES obtained from Sigrna Chemical Company (Cat. No. M-8250) in deionized water.

Figure 5:
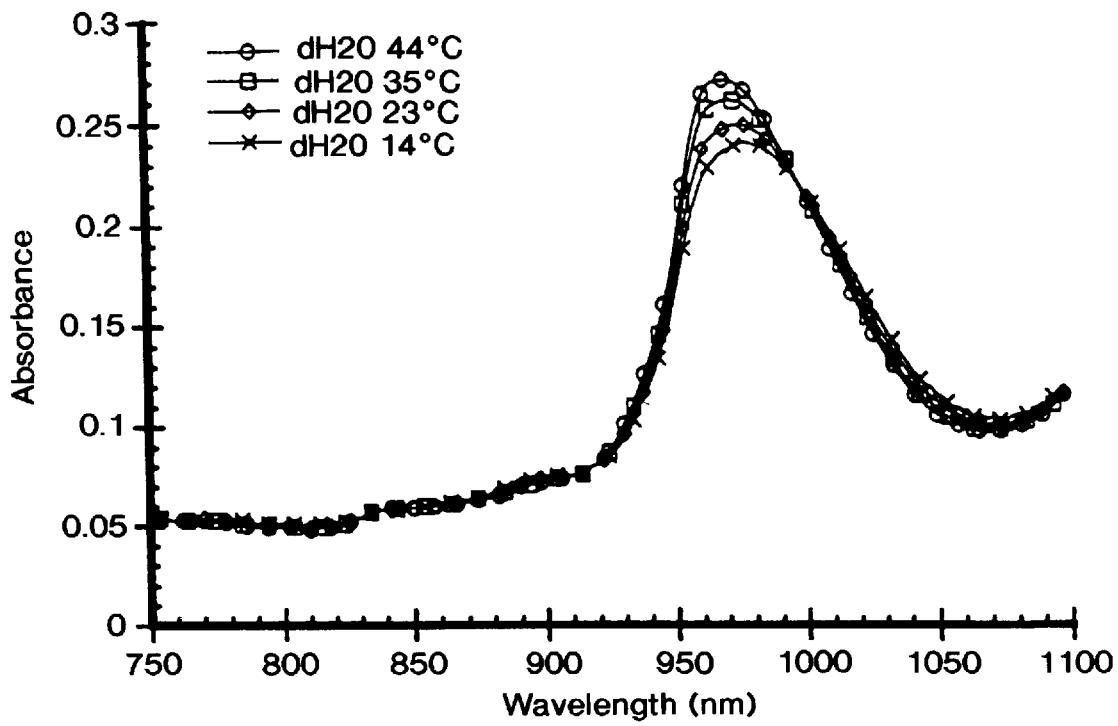
FIG. 5 is a graph showing the absorption spectrum of pure water between 750 nm and 1100 nm at four different temperatures.

FIG. 5 shows the absorption spectrum of pure water between 750 and 1100 nanometers at 4 different temperatures, i.e. 14° C., 23° C., 35° C. and 44° C. The spectra were taken in an ATI Unicam UV-2-100 Double Beam Scanning UV-Visible Spectrometer with a 2.0 nanometer fixed bandwidth. The data were taken under the control of a Compaq 386 computer running ATI Vision software set to take spectral data in the "Survey" mode at "Intelliscan" speed. Approximately 3 ml samples were placed in Spectro Clear™ Acrylic precision spectrophotometer cuvettes, with a light absorption pathlength of 1.00 cm, obtained form Centaur Science, Inc., Stamford, Conn., (Cat. No. SCA-20) in the sample beam of the spectrophotometer. The reference beam contained no sample or cuvette. (Measurements made in this configuration are said to employ an "air blank").

FIG. 5 also shows that between 900 and 917 nanometers there is relatively little absorbance of the water sample. Between 960 and 980 nanometers there is a peak of maximal absorbance of the water sample. The wavelength of maximal absorbance ($\lambda_{max}$), as well as the absorbance at $\lambda_{max}$, changes as a function of temperature. For example, at 974 nanometers which is near $\lambda_{max}$, the absorbance changes by about 0.4% per degree centigrade. Thus, in order to obtain +/−1% precision in determination of optical pathlength, the temperature must vary by no more than +/−2.50° C.

In contrast, at about 998 nanometers pure water gave constant optical density of about 0.14 at all four temperature values. Thus, the wavelength region near 998 nanometers (e.g. the wavelength region from 988 to 1008 nanometers) is a region where optical properties of pure water are nearly independent of temperature. For the present, we shall call such a wavelength region an "isosbestic wavelength region"

which for pure liquid water occurs near 998 nanometers as a function of temperature.

Figure 6:
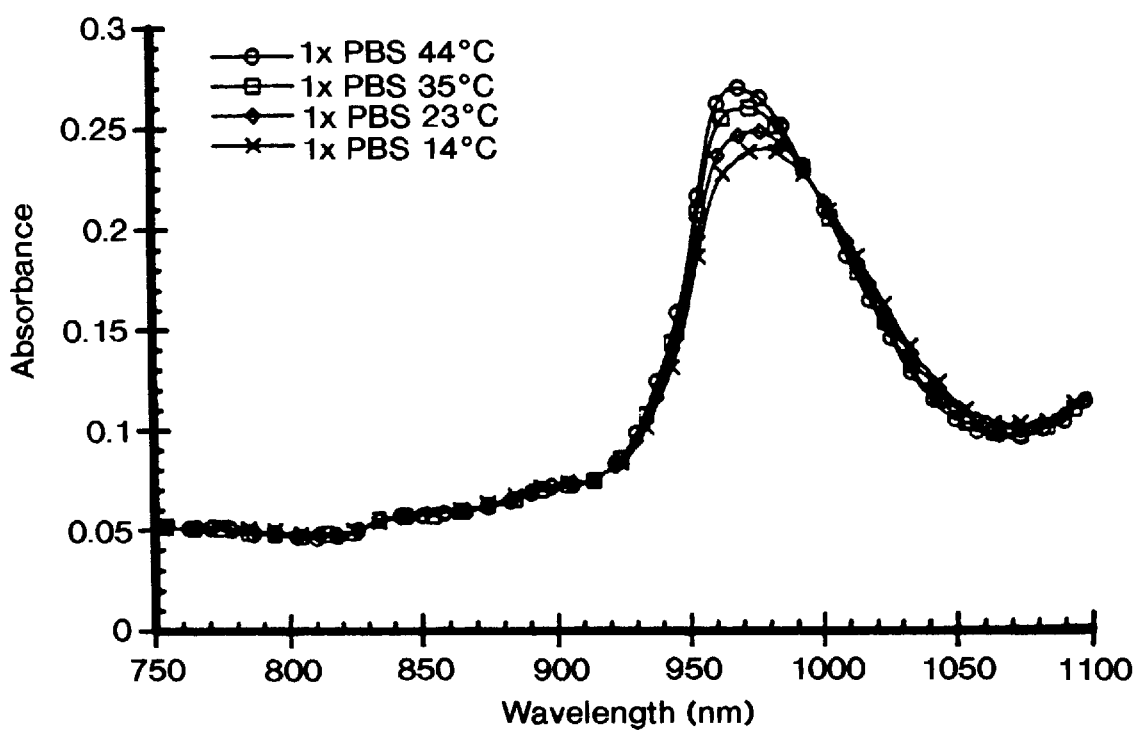
FIG. 6 is a graph of the near infrared (NR) portions of the electromagnetic spectrum for a biological buffer solution, Dulbecco's phosphate-buffered saline (PBS).

FIG. 6 similarly shows the NR absorption spectrum of Dulbecco's phosphate-buffered saline (PBS) containing 200 mg/l potassium chloride, 200mg/l potassium phosphate monobasic, 8000 mg/l sodium chloride and 1158 mg/l sodium phosphate dibasic, pH 7.23 which is a commonly-used biological buffer solution. The absorption spectrum is strikingly similar to that of pure water seen in FIG. 5. The NIR absorption spectrum for isotonic (0.155 M) sodium chloride; 0.1 M phosphate, pH 7.0 and 0.1 M TRIS, 0.1 M HEPES, 0.1 M MES and Threshold Assay Buffer similarly were recorded at 14° C., 23° C., 35° C. and 44° C. In each case the NIR absorption spectra (not shown) are virtually indistinguishable from that of pure water (i.e. less than 3% different in relative absorption intensity any wavelength). The isosbestic behavior, as a function of temperature, in each case is observed near 998 nanometers.

Table III shows optical density values, determined at several selected wavelengths, each at the 4 selected temperature values, for each aqueous buffer solution. Also shown in Table III are the results of taking the difference in optical density measured at 998 nanometers and optical density measured at either 900 or 910 nanometers, i.e., ($OD_{998}$–$OD_{900}$) or ($OD_{998}$–$OD_{910}$) for each aqueous buffer solution at each temperature. The results show that for the 8 different samples, the ($OD_{998}$ and $OD_{900}$) and ($OD998$–$OD_{910}$) were remarkably constant at all temperature values. The ($OD_{998}$–$OD_{900}$) values ranged from 0.138 to 0.133, i.e. a range of 3.6%. The ($OD_{998}$–$OD_{910}$) values ranged from 0.135 to 0.132. i.e. a range of 2.9%. Thus interference or inaccuracies in determining optical pathlength though liquid samples can be eliminated substantially by:

1.) measuring a first optical density value of the samples in a first "isosbestic wavelength region",
2.) measuring a second optical density value of the samples in a second "isosbestic wavelength region", and
3.) determining the difference in the first and second optical density values.

Preferably, the absorption coefficient of the sample is substantially different in the first and second wavelength regions. For example, as shown in FIGS. 5 and 6 and Table III, for aqueous samples a "isosbestic wavelength region" occurs about 998 nanometers (generally from 993 to 1002 nanometers, and more generally from 988 to 1008 nanometers). A second isosbestic wavelength region occurs about 910 nanometers (generally from 900 to 910 nanometers, and more generally from 750 to 930 nanometers). Alternatively, a second isosbestic wavelength region occurs near 1090 nanometers (generally from 1080 to 1100 nanometers and more generally from 1050 to 1150 nanometers).

TABLE 3

|  | dH20 | 0.9% NaCl (Saline) | 0.1 M HEPES | 1xThreshold Assay Buffer | 0.1 M TRIS | 1xPBS | 0.1 M Phosphate Buffer | 0.1 M MES |
|---|---|---|---|---|---|---|---|---|
| 14° C. | | | | | | | | |
| 900 | 0.075 | 0.072 | 0.072 | 0.070 | 0.074 | 0.072 | 0.071 | 0.076 |
| 910 | 0.075 | 0.073 | 0.073 | 0.071 | 0.075 | 0.073 | 0.072 | 0.077 |
| 974 | 0.240 | 0.237 | 0.235 | 0.236 | 0.238 | 0.238 | 0.236 | 0.239 |
| 976 | 0.241 | 0.239 | 0.236 | 0.237 | 0.239 | 0.239 | 0.237 | 0 240 |
| 978 | 0.242 | 0.239 | 0.236 | 0.237 | 0.239 | 0.239 | 0.237 | 0.241 |
| 980 | 0.241 | 0.239 | 0.236 | 0.237 | 0.239 | 0.240 | 0.237 | 0.240 |
| 982 | 0.240 | 0.238 | 0.235 | 0.236 | 0.239 | 0.239 | 0.237 | 0.240 |
| 998 | 0.222 | 0.220 | 0.218 | 0.217 | 0.221 | 0.220 | 0.218 | 0.222 |
| 1000 | 0.219 | 0.216 | 0.214 | 0.214 | 0.218 | 0.217 | 0.215 | 0.219 |
| 998–900 | 0.147 | 0.148 | 0.146 | 0.147 | 0.147 | 0.148 | 0.147 | 0.146 |
| 998–910 | 0.147 | 0.147 | 0.145 | 0.146 | 0.146 | 0.147 | 0.146 | 0.145 |
| 23° C. | | | | | | | | |
| 900 | 0.073 | 0.072 | 0.072 | 0.069 | 0.073 | 0.072 | 0.071 | 0.075 |
| 910 | 0.075 | 0.072 | 0.073 | 0.070 | 0.074 | 0.073 | 0.072 | 0.076 |
| 974–976 | 0.250 | 0.248 | 0.245 | 0.246 | 0.248 | 0.248 | 0.247 | 0.249 |
| 976 | 0.250 | 0.248 | 0.245 | 0.246 | 0.249 | 0.249 | 0.247 | 0.250 |
| 978 | 0.250 | 0.248 | 0.245 | 0.245 | 0.249 | 0.248 | 0.246 | 0.249 |
| 980 | 0.249 | 0.247 | 0.244 | 0.245 | 0.247 | 0.247 | 0.245 | 0.248 |
| 982 | 0.247 | 0.245 | 0.243 | 0.243 | 0.246 | 0.246 | 0.244 | 0.247 |
| 998 | 0.223 | 0.220 | 0.218 | 0.218 | 0.222 | 0.221 | 0.219 | 0.222 |
| 1000 | 0.219 | 0.216 | 0.214 | 0.214 | 0.218 | 0.216 | 0.215 | 0.219 |
| 998–900 | 0.150 | 0.148 | 0.146 | 0.149 | 0.149 | 0.149 | 0.148 | 0.147 |
| 998–910 | 0.148 | 0.148 | 0.145 | 0.148 | 0.148 | 0.148 | 0.147 | 0.146 |
| 35° C. | | | | | | | | |
| 900 | 0.073 | 0.071 | 0.072 | 0.069 | 0.073 | 0.071 | 0.071 | 0.074 |
| 910 | 0.075 | 0.072 | 0.073 | 0.070 | 0.074 | 0.072 | 0.073 | 0.076 |
| 974 | 0.262 | 0.259 | 0.256 | 0.258 | 0.260 | 0.260 | 0.260 | 0.262 |
| 976 | 0.262 | 0.259 | 0.256 | 0.257 | 0.260 | 0.260 | 0.259 | 0.261 |
| 978 | 0.260 | 0.258 | 0.255 | 0.256 | 0.259 | 0.258 | 0.258 | 0.260 |
| 980 | 0.258 | 0.256 | 0.253 | 0.254 | 0.256 | 0.256 | 0.255 | 0.257 |
| 982 | 0.256 | 0.253 | 0.250 | 0.251 | 0.254 | 0.253 | 0.253 | 0.255 |
| 998 | 0.223 | 0.220 | 0.218 | 0.218 | 0.222 | 0.220 | 0.220 | 0.222 |
| 1000 | 0.218 | 0.215 | 0.213 | 0.213 | 0.217 | 0.216 | 0.215 | 0.217 |

TABLE 3-continued

|  | dH20 | 0.9% NaCl (Saline) | 0.1 M HEPES | 1xThreshold Assay Buffer | 0.1 M TRIS | 1xPBS | 0.1 M Phosphate Buffer | 0.1 M MES |
|---|---|---|---|---|---|---|---|---|
| 998–900 | 0.150 | 0.149 | 0.146 | 0.149 | 0.149 | 0.149 | 0.149 | 0.148 |
| 998–910 | 0.148 | 0.148 | 0.145 | 0.148 | 0.148 | 0.148 | 0.147 | 0.146 |
| 44° C. | | | | | | | | |
| 900 | 0.073 | 0.070 | 0.071 | 0.069 | 0.072 | 0.071 | 0.071 | 0.074 |
| 910 | 0.075 | 0.072 | 0.072 | 0.071 | 0.074 | 0.072 | 0.072 | 0.076 |
| 974 | 0.271 | 0.268 | 0.265 | 0.266 | 0.269 | 0.268 | 0.268 | 0.270 |
| 976 | 0.269 | 0.266 | 0.264 | 0.265 | 0.267 | 0.267 | 0.267 | 0.269 |
| 978 | 0.267 | 0.264 | 0.262 | 0.263 | 0.266 | 0.265 | 0.264 | 0.267 |
| 980 | 0.265 | 0.262 | 0.259 | 0.260 | 0.263 | 0.262 | 0.261 | 0.264 |
| 982 | 0.261 | 0.258 | 0.256 | 0.257 | 0.259 | 0.259 | 0.258 | 0.260 |
| 998 | 0.222 | 0.220 | 0.218 | 0.218 | 0.222 | 0.220 | 0.219 | 0.222 |
| 1000 | 0.217 | 0.214 | 0.212 | 0.212 | 0.216 | 0.215 | 0.214 | 0.216 |
| 998–900 | 0.149 | 0.150 | 0.147 | 0.149 | 0.150 | 0.149 | 0.148 | 0.148 |
| 998–910 | 0.147 | 0.148 | 0.146 | 0.147 | 0.148 | 0.148 | 0.147 | 0.146 |

When employing ($OD_{998}$–$OD_{910}$) values to measure optical pathlength, a value of 0.135 cm$^{-1}$ (generally from 0.140 to 0.130 cm$^{-1}$) may be used to calculate optical pathlength through substantially aqueous samples. For example, if a (OD998–$OD_{910}$) value of 0.135 is determined for aqueous samples with an unknown optical pathlength, the unknown optical pathlength is calculated to be 0.135/0.135 cm$^{-1}$, i.e. 1 cm. Similarly, if an (OD998–$OD_{910}$) value of 0.135 is determined, then the unknown optical pathlength is 0.100/0.135 cm$^{-1}$, i.e. 0.741 cm. As another example, optical pathlengths through substantially aqueous samples may be determined from any measured ($OD_{998}$–$OD_{900}$) value by employing the constant 0.137 cm$^{-1}$ (instead of 0.135 cm$^{-1}$) in a similar fashion. As a third example, optical pathlengths through substantially aqueous samples may be determined from any measured ($OD_{998}$–$OD_{1090}$) value by employing the constant 0.110 cm$^{-1}$ in a similar fashion. It will be recognized by those skilled in the art of photometry that any constant so determined for any predetermined mixture of aqueous and nonaqueous solvents, may be used (together with measurement of the NIR absorbance properties of the predetermined mixture) for determination of any unknown optical pathlength for the mixture.

EXAMPLE 7

Elimination of Error in Determination of Optical Pathlength due to Variation in Solvent Composition In this example, NIR absorption spectra, between 750 and 1100 nanometers, were acquired as described in Example 6. The samples were maintained near room temperature (at about 20 to 25° C.).

Figure 7:
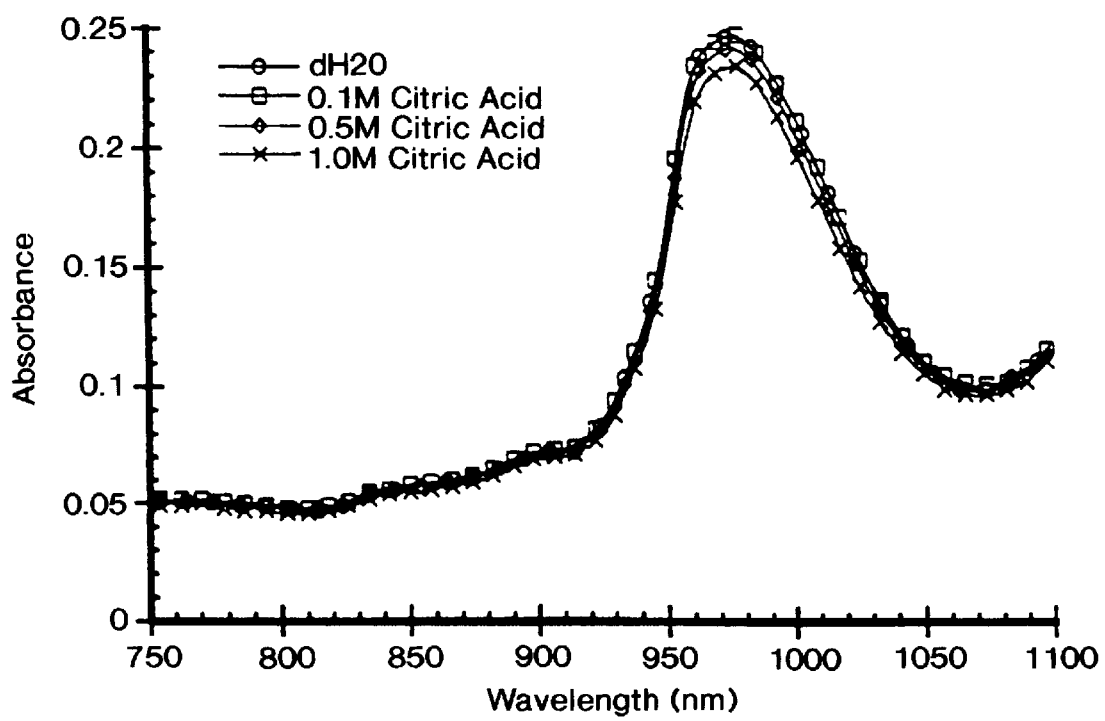
FIG. 7 is a graph of the results of the near infrared (NIR) portion of the electromagnetic spectrum for pure water and 0.1M, 0.5M and 1.0M citric acid solutions in pure water.

FIG. 7 shows the NIR absorption spectra of pure water, 0.1 M, 0.5 M, and 1.0 M citric acid solutions (in water). The citric acid solutions show relatively insignificant deviation from the spectrum of water at the lowest, 0.1 M concentration. The deviation however increases with increasing concentration and is greatest at the highest (1.0 M) citrate concentration.

Figure 8:
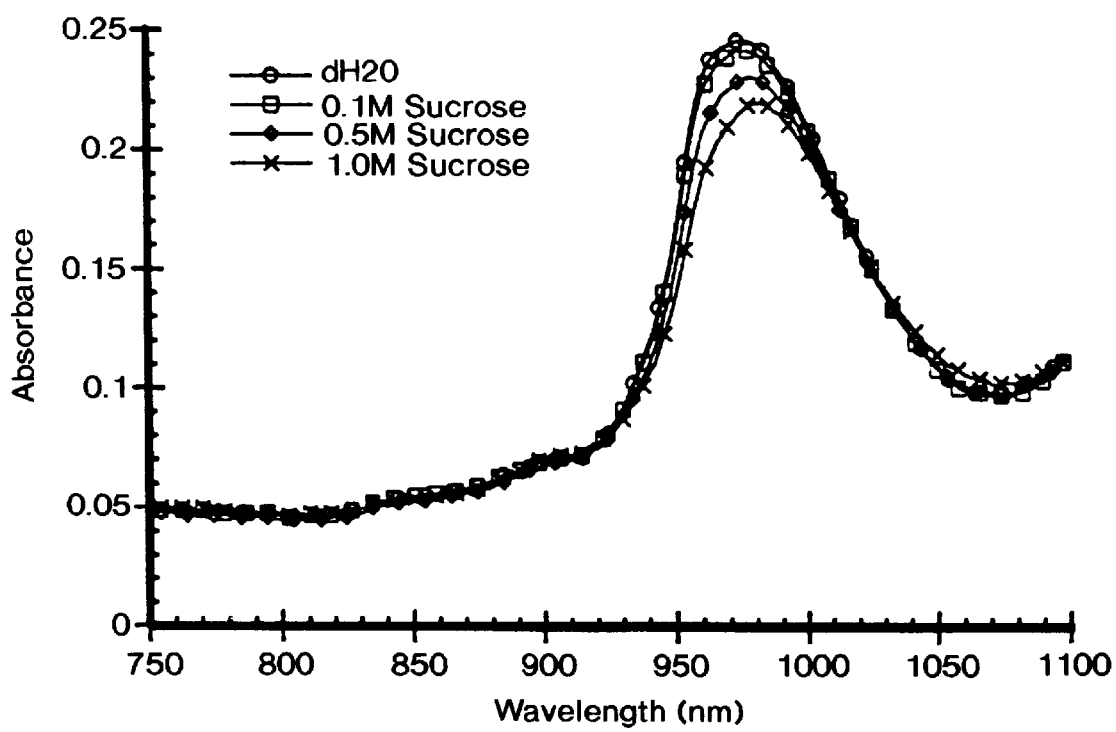
FIG. 8 is a graph of the results of the near infrared (NIR) portion of the electromagnetic spectrum, between 750 nm and 1100 nm, of either pure water, 0.1M, 0.5M or 1.0M sucrose solutions in pure water.

FIG. 8 similarly shows the NIR absorption spectra, between 750 and 1100 nanometers, of either pure water, 0.1 M, 0.5 M, or 1.0 M sucrose solutions (in pure water). Similar to the citric acid solutions, the sucrose solutions show relatively insignificant deviation from the spectrum of pure water for the lowest, 0.1 M concentration. As for citrate, however, the deviation increases with increasing solute concentration and is greatest at the highest (1.0 M) concentration. The deviation caused by sucrose is slightly more pronounced than that caused by citrate. The value of ($OD_{970}$–$OD_{910}$) is about 20% less for 1.0 M sucrose compared to pure water. Significantly better, the value of either ($OD_{998}$–$OD_{910}$) or ($OD_{998}$–$OD_{910}$) are only about 9% less for 1.0 M sucrose compared to pure water. While significant improvement in determining optical pathlength is obtained by measuring absorption of light in the "isosbestic wavelength region" near 998 nanometers, substantially complete elimination of error in such determinations, with all aqueous samples, however, is not possible.

EXAMPLE 8

Incorporation of a Reference Solvent Liquid of Known Optical Pathlength

In order to substantially eliminate errors in determination of unknown optical pathlength of sample solutes dissolved at high concentration in a solvent liquid, an improved method with the following steps is employed:

1. Place a reference comprising a reference sample solvent in a known optical pathlength, and a sample, comprising a sample in the sample solvent, in an unknown optical pathlength, and
2. Measure:
    a) a first optical density value ($A_{REF\lambda 1}$) of the reference sample solvent at a first preselected wavelength in the NIR where the sample analyte does not absorb light substantially and where absorption of light by the sample solvent is near a local maximum (for example in the region of 950 to 1000 nanometers for an aqueous solvent), and
    b) a second optical density value ($A_{REF\lambda 2}$) of the reference sample solvent at a second preselected wavelength in the NIR where neither the sample analyte nor the reference sample solvent absorb light substantially (for example in the region of 900 to 910 nanometers, or the region from 1060 to 1080 nanometers, for an aqueous solvent), and
    c) a third optical density value ($A_{SMP\lambda 1}$) of the sample at the first preselected wavelength, and
    d) a fourth optical density value ($A_{SMP\lambda 2}$) of the sample at the second preselected wavelength, and 3. Calculate the optical pathlength as:

$$\text{Sample Light Absorption Pathlength} = \quad (12)$$

$$\frac{\text{Reference Light Absorption Pathlength}(A_{SMP\lambda1} - A_{SMP\lambda2})}{(A_{REF\lambda1} - A_{REF\lambda2})}$$

EXAMPLE 9

A Device Incorporating A Reference Solvent Liquid of Known Optical Pathlength

Advantageously, a device will enclose both the reference and the sample so that the temperature of the reference and the sample will be substantially the same temperature, generally within a range of 2° C. and more generally with a range of 5° C. Also advantageously, the device will enclose a multiplicity of samples, e.g. an 8×12 array of samples in a 96-well multiassay plate, at a multiplicity of sample sites maintained at substantially the same temperature as the reference. A preferred embodiment of the present invention is herein described. The device was used in following method steps 1–3 and Equation 4 and 5 in Example 2. The device measures unknown optical pathlengths of a multiplicity of assay sites with the aid of an incorporated reference liquid of known optical pathlength. In operation, a user performs the following operations:

(a.) The reference liquid is placed in a cuvette, of known optical pathlength, within the device. The reference liquid is preselected to be similar in solvent composition and temperature to the samples. (Optimally but not required, the sample analyte will be present in the reference liquid.)

(b.) Next, the samples on a multiassay plate, are placed in the device so that the samples and the reference liquid are maintained at substantially the same temperature (to within 1–2° C.).

(c.) The device measures the transmission of NIR light through each of the liquid samples and through the reference liquid of known optical pathlength.

(d.) The device compares the transmission of light through both the samples and the reference liquid and calculates the optical pathlength of the samples.

Having determined the optical pathlength through each of the samples in a multi-assay plate, the device also may be used to determine the concentration of analytes in such samples by determining the absorbance of the analytes at a preselected wavelength. The results of such determinations, therefore, may now be expressed in terms of optical density per unit pathlength, e.g. $A \cdot cm^{-1}$. Customarily the results will be expressed in optical density per 1 cm pathlength. For example, if the sample material absorbs at 405 nanometers wavelength and the optical density of the sample at 405 nanometers, $A_{405}$, if determined by the device to be 0.150 O.D. units; and the optical pathlength of the sample, determined by steps a–d above is determined to be 0.5 cm, then the calculated $A_{405} \cdot cm^{-1}$ value will be 0.300.

Once the optical pathlength is known, the concentration of analyte may be determined by Beer-Lambert Law given in equation (1), from the extinction coefficient $\epsilon_\lambda$ at a preselected wavelength $\lambda$.

Figure 9:
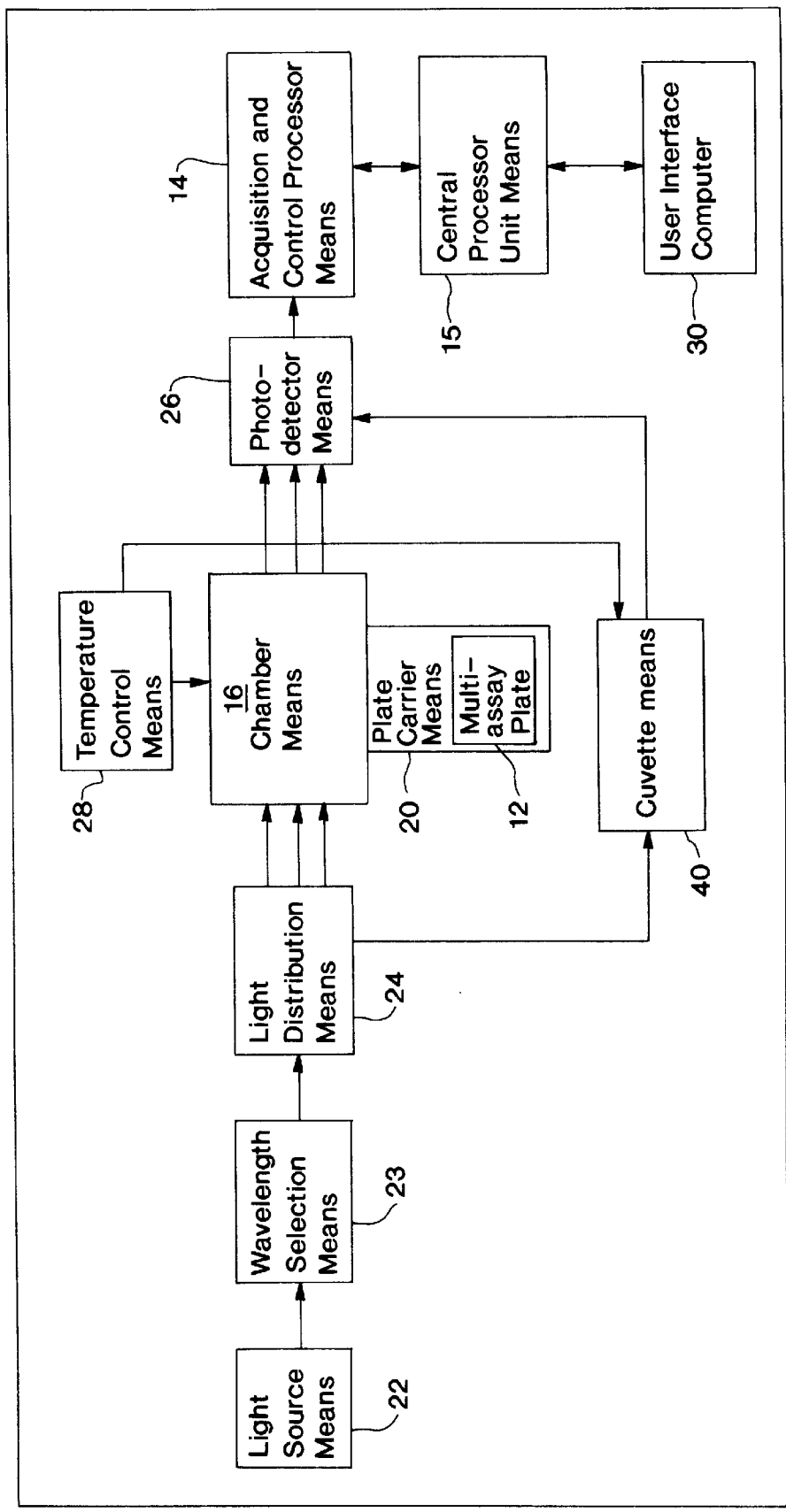
FIG. 9 is a schematic representation of the device of the present invention.

Shown in FIG. 9 is a photometric measuring system 10 for monitoring the optical characteristics of a multiplicity of samples contained on a multiassay plate 12 having multiplicity of sample sites with variable optical pathlength. The system has at least one reference site of known optical pathlength. The system 10 is comprised of a light source means 22 which directs light to a wavelength selection means 23, which causes a substantially monochromatic band of light to pass into a light distribution means 24. The light distribution means 24 directs light to:

a) a means for retaining a reference optical pathlength of known pathlength, shown in FIG. 9 as a cuvette means 40. Light transmitted through the reference optical pathlength is detected by a photodetector means 26, and b) a chamber means 16 which encloses the multiplicity of sample sites.

The multi-assay plate 12 is carried by a plate carrier means 20 so as to position the sample sites so that light directed by the light distribution means 24, and transmitted by the samples is detected by the photodetector means 26. A temperature control means 28 controls the temperature within the chamber means 16 and the cuvette means 40.

Electrical signals from the photodetector means 26 are sent to an acquisition and control processor means 14 which is in electrical communication with a central processor unit means 15. The central processor means 15 may send data directly to a printer and be controlled by a user. Advantageously, however, the central processor means 15 will be interfaced to a user interface computer 30, which enables the user to control the system 10, acquire data, visualize data, compute data parameters from the acquired data, and ultimately to export the data or parameters to an external printing device.

Figure 10:
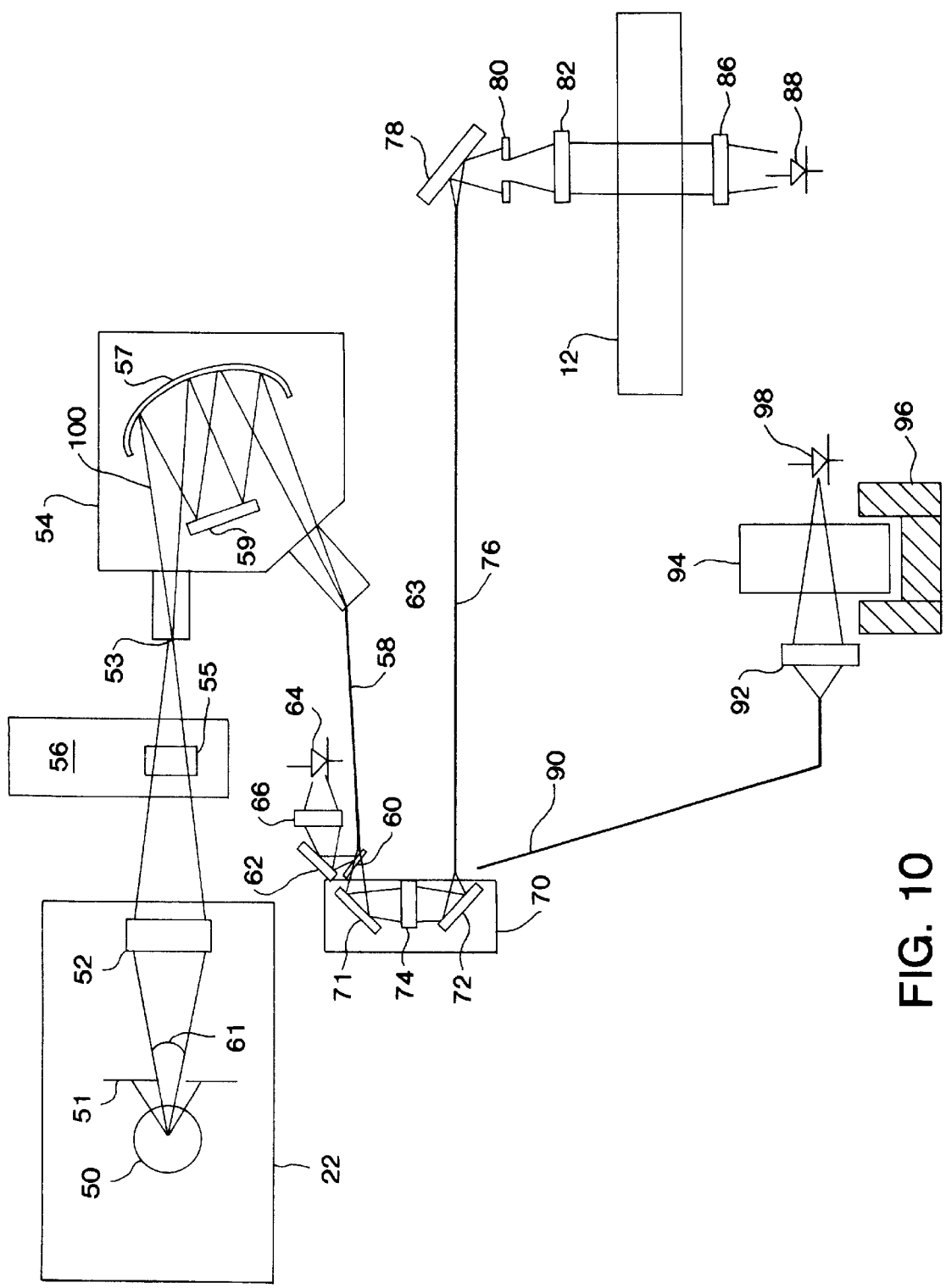
FIG. 10 is a schematic representation of a preferred embodiment of the present invention.

FIG. 10 is a detailed description of a preferred embodiment of the photometric measuring system 10. Except for the disclosure given below, the preferred embodiment is identical to the preferred device disclosed in U.S. patent application Ser. No. 08/228,436 filed Apr. 15, 1994 which is incorporated herein by reference. The system 10 produces a beam of substantially monochromatic light, in the form of flashes, and delivers this light sequentially to a plurality of light channels, eight in the preferred embodiment, to sequentially illuminate the fluid sample in the multiassay plate 12.

An excitation light source 50, such as a xenon flash lamp, emits light flashes containing wavelengths between at least 200 nanometers and 1100 nanometers. Light from the excitation light source 50 beams through an aperture 51 limiting the light arc (61) to approximately ten degrees (10°). This light then passes through a source lens 52, which focuses the light through one of a series of filters 55, included on a filter wheel 56, upon a monochrometer, generally designated 54. The excitation light source 50, aperture 51, and source lens 52 cooperate to define the lights source means 22.

The source lens 52, in this preferred embodiment is a fused silica plano-convex lens with a 12.7 millimeter diameter, a 16 millimeter focal length, and an optical magnification of 1×. The source lens 52 is spaced 32 millimeters from the excitation light source 50 and 32 millimeters from the entrance slit 53 where light enters the monochrometer 54. A collimating/focusing mirror 57 reflects and collimates the light beam onto a rotatable diffraction grating 59. There the light is dispersed at an angle with respect to the grating. This angle is dependent upon the wavelength of light striking the grating. The dispersed light falls back on the collimating/focusing mirror 57 which focuses substantially monochromatic light, within a narrow wavelength band, upon an exit slit 63. Thus, the wavelength range (bandpass) of substantially monochromatic light passing through exit slit 63 is dependent upon the wavelength of light and the angle of the grating 59 with respect to the collimated light beam. The wavelength of maximal intensity of light passing through the exit slit may be preselected by rotating the grating 59 with respect to the incident light coming from mirror 57. The bandpass of monochromatic light passing through exit slit 63 is dependent principally upon the optical distance from grating 59 to exit slit 63, as well as the widths of exit slit 63, entrance slit 53 and aperture 51.

Exit slit 63 preferably, 0.7 in width and 1.3 millimeters in height, is formed by a metal end cap forming the end of a bundle of optical fibers 58 which accepts the substantially monochromatic light. Cooperating to define the wavelength selection means 23 are filter wheel 56, optical filters 55, and monochrometer 54. The output of monochromator 54 provides light having a predetermined, continuously selectable, second wavelength range within the first wavelength range provided by light source 50. In the preferred embodiment disclosed herein, the second wavelength range has a predetermined bandpass width, defined as the wavelength width at one-half maximum light transmission, of about 2 nanometers for all center-band wavelengths continuously selectable by the user between 250 and 750 nanometers. The bandpass width may be predetermined within a range of about 1 to 20 nanometers by changing the width of the exit slit 63, e.g. by employing a mechanically adjustable slit as the exit slit 63.

In the preferred embodiment optical fiber bundle 58 includes nineteen (19) optical fibers each 200 microns in diameter with a numerical aperture of 0.22, each arranged at the input in three (3) rows of six (6), seven (7), and six (6) fibers. This effectively defines a 0.7 millimeter by 1.3 millimeter rectangular exit slit 63. The output of the optical fiber 58 is configured as a circle with a diameter of 1.3 millimeters. Light from the output of fiber 58, which is emitted over a solid angle of about ten degrees, is split by a beam splitter 60, a sapphire window in this preferred embodiment. The beam splitter 60 splits the light into a test light that passes through the beam splitter 60 to a rotor assembly 70 and a reference light that reflects from the beam splitter 60 to a flat reference mirror 62. The reference mirror 62 reflects the reference light through a reference lens 66 to a reference photodetector 64 of the photodetector means 26. The reference lens 66 is a bi-convex lens, is made of fused silica, has a focal length of 6.8 millimeters, and has a diameter of 6.8 millimeters.

The intensity of light flashes emitted by the Xenon flash light 50 may vary by as much a 50% between successive flashes due to variations in the energy and position of the flash arc within the flash lamp. The reference photodetector 64 outputs an electrical signal; representative of the amplitude of the monochromatic light carried by the optical fiber 58 for each flash of the light excitation source 50. This electrical signal is used as an intensity reference for the reading of sample light transmitted through samples in the multi-assay plate 12.

The rotor assembly 70 includes two substantially identical rotor mirrors 71 and 72 to redirect the light by 180° (degrees) (each mirror reflects light by 90°) and a rotor lens 74 to focus the light beam between the rotor mirrors 71 and 72. The rotor mirrors 71 and 72 and rotor lens 74 act to reduce the spot size of the light beam from 1.3 millimeter diameter at the input of the rotor assembly 70, which is the output of the optical fiber 58, to 0.65 millimeters at the output, which is the input of a selected one of nine (9) receiving optical fibers 76 or the input of a reference distribution optical fiber 90. The reduction in light beam diameter within the rotor 70 allows substantially all of the light to be launched at a solid angle of about 20° into the receiving fibers 76 of the light distribution means 24, greatly enhancing efficiency of sample light transmitted through the rotor 70. Care is taken so that the sample light is not focused in such a way that it exceeds the numerical aperture of the receiving optical fibers 76 and 90 which will accept light over a solid angle of about 24°.

The optical distribution channels are defined by the receiving optical fibers 76 and 90, made of solid silica or quartz, 1 millimeter in diameter, with a numerical aperture of 0.22. Light from the sample distribution optical fibers 76 reflects off a sample light mirror 78, made of $MgF_2$ with a flat surface, into a substantially vertical sample light distribution direction. A sample light aperture 80 further limits the numerical aperture of the light beam. A sample light lens 82 and a sample light photodetector lens 86, each a biconvex lens made of fused silica with a 6.8 millimeter focal length and a 6.8 millimeter diameter, further focus the sample light. For ease of illustration, FIG. 10 shows only one of a series of eight substantially identical sample light distribution optical fibers 76, sample light mirrors 78, sample light apertures 80, sample light lenses 82 and sample light photodetector lenses 86.

A reference pathlength distribution optical fiber 90 directs reference pathlength light from optical rotor 70 to reference pathlength lens 92, through a reference cuvette of known optical pathlength 94, which is retained in place by a cuvette holder 96. Customarily photometric measuring system 10 provides cuvette holder 96 without cuvette 94. During use of the invention, the user selects an appropriate reference cuvette which may be made of quartz, glass, polystyrene, polymethacylate or other suitable transparent material. Cuvette 94 and cuvette holder 96 cooperate to define cuvette means 40. Reference pathlength light transmitted through cuvette 94 is detected by reference pathlength photodetector 98.

In operation, first a reference sample solvent is placed in the reference cuvette of known optical pathlength (e.g. a 1.00 cm optical pathlength) and samples in the sample solvent are placed in one, or more, wells of the multi-assay plate 12. The multi-assay plate is then placed on a plate carrier means 20 within chamber means 16. The user instructs the system 10 to "read" one-or-more preselected samples. The plate carrier means positions the preselected samples between the sample light lenses 82 and sample light photodetector lenses 86 so that light from the sample distribution optical fibers 76 will pass substantially vertically through the samples without striking the side-walls of the multi-assay plate, which contains the samples.

In a reading cycle the rotor assembly 70 first rotates so as to distribute light to a dark channel, so that no light falls upon sample photodetectors 88 or pathlength reference photodetector 98 when light source 50 emits a flash of light. Electrical signals from sample photodetectors 88 and pathlength reference photodetector 98 provide a zero light baseline value for each photodetector when the light is distributed to a dark channel. The rotor assembly 70 secondly rotates so as to distribute reference pathlength light through the reference cuvette 94, which contains reference sample solvent in a known optical pathlength. The reference cuvette is retained in place by a cuvette holder 96. Reference pathlength light transmitted through cuvette 94 is detected by reference pathlength photodetector 98 which, in turn, sends an electrical signal related to the intensity of detected light to acquisition and control processor means 14.

The rotor assembly 70 next rotates to sequentially illuminate the series of eight sample light distribution optical fibers 76 so as to sequentially illuminate the fluid samples in the multiassay plate 12. The multiplicity of samples receives sample light having a substantially identical spectral distribution of light intensity provided by monochrometer 54. The photometric device 10 described provides the above sample light characteristics to a multiplicity of samples in a multi-assay plate within short periods of times so that the optical properties of 96 samples contained in a conventional 8×12 microplate may be determined within approximately 9 seconds (generally from 8 to 10 seconds). Determination of optical pathlength requires measurement at, at least 2 different wavelengths, λ1 and λ2. Thus, in order to measure optical pathlength through the samples the measurement procedure is first performed at λ1 and then repeated at λ2, thus the measurements is completed within 18 seconds (generally from 16 to 20 seconds). Optionally, the reading process may be adjusted to proceed at a slower pace (for example over 10 minutes or more) when there is no need for rapid determinations.

EXAMPLE 10

Elimination of Error in Determination of Absorbance of Samples per Unit Optical Pathlength The device disclosed in Example 9 may be used to substantially eliminate error in the determination of the ratio of absorbance of analytes within liquid samples and the optical pathlength. These ratiometric measurements are given as "Light Absorbance per Unit Pathlength" in Examples 2 and 3 above.

In order to perform such ratiometric measurements, the device additionally monitors the absorbance of an analyte, in the one or more samples sequentially, at a preselected wavelength. This value is given as "Sample $A_x$," in examples 2 and 3 above. The device then computes the ratio of Sample $A_x$, and the optical pathlength, for each sample, to give "Light Absorbance per Unit Pathlength".

The examples below show further methods resulting in improved precision in determination of light absorbance by an analyte dissolved in a solvent by using vertical-beam photometry.

EXAMPLE 11

Methods for Improving Precision of Optical Pathlength Determination in a Vertical-Beam Photometer 1. Evaluation of precision was carried out with SPECTRAmax®PLUS microplate spectrophotometer. For these evaluations 200 μl of 0.05 M potassium phosphate buffer, adjusted to pH 7.00 with NaOH (and containing yellow food coloring as the test analyte) was dispensed in the wells of a quartz, 96-well microplate (available from Molecular Devices as Part Number R8024). The test analyte solution is available from Fisher Scientific as Catalog Number SB107-500 (pH 7.00 Buffer Solution).

The test analyte solution has a broad spectral absorption maximum between 420 and 440 nanometers which returns close to a baseline value between 510 to 520 nanometers. The wavelength for determining analyte absorbance was selected to be 420 nanometers near the absorption maximum. Precision absorbance studies were performed in 96 replicate wells of the quartz microplate. The test analyte was dispensed into the microplate wells and analyte absorbance per unit solvent pathlength was measured in each well. Two method variables were evaluated in all four possible combinations for effect on measurement precision. The first variable was to determine the absorbance of the analyte at a single wavelength ($A_{420}$) (single wavelength mode) or at dual wavelengths ($A_{420}-A_{520}$) (dual wavelength mode). In the dual wavelength mode, the second absorbance value ($A_{520}$) is used as a reference absorbance measurement. In all cases, absorbance of the solvent was measured at two wavelengths (1000 and 900 nanometers) in order to determine optical pathlength of the solvent. Thus, at least three absorbance values are always determined at at least three different wavelengths. Light Absorbance per Unit Pathlength is then calculated as: $0.1433(A_{420})/(A_{1000}-A_{900})$ or alternatively $0.1433(A_{420}-A_{520})/(A_{1000}-A_{900})$.

In practice, the absorbance of each sample in the multi-assay plate (in this case a 96-well microplate) was measured at 420, 520, 900 and 1000 nanometers. A second method variable was to (A) measure all absorbances values in each individual sample at all preselected (in this case three or four) wavelengths without moving the samples (a "Stationary Read"). This was accomplished, in this example, by selecting 420, 520, 900 and 1000 nanometers bandpass light, sequentially, with monochrometer 54 for each sample before moving the microplate 12 with plate carrier means 20. Alternatively, other methods of spectral scanning without sample movement, such as emplying a diode-array detector together with a spectral dispersion means such as a prism, grating, tunable optical fillers, array of optical fillers, etc., may be used. In the alternative (B) of the second method variable, absorbance values are measured on all samples at a first wavelength (by moving the samples), switching to a second wavelength by adjusting the monochrometer and measuring absorbances values on all samples at the second wavelength (again by moving the samples), and repeating the process until all absorbance values, at all selected wavelength values, have been determined. In both cases repositioning of the multi-assay is performed by the motorized plate carrier which centrally positions the sample wells under the light paths of the fiber optic channels.

Table IV gives the results of a precision test using the four combinations of the two method variables. Dual wavelength absorbance measurements gave greater precision (less error) than single wavelength absorbance measurements. Also, absorbance measurements using multiple wavelengths gave the greatest precision when measurements were made at all the wavelengths prior to moving the fluid samples ("Stationary Read"). The lowest error was observed when dual wavelength absorbances were carried out in combination with a Stationary Read. In that case, the standard deviation of Absorbance/cm Pathlength measurements was 0.003 absorbance units per cm (coefficient of variation= 0.8%). In contrast when single wavelength absorbance measurements were made and the samples were not stationary, the standard deviation of Absorbance/cm Pathlength measurements was 0.008 absorbance units per cm (coefficient of variation=2.1%).

TABLE IV

Error in Determination of Analyte Absorbance
per Unit Optical Pathlength

|  | Stationary | Non Stationary |
|---|---|---|
| $A_{420}-A_{520}$ | *0.003 | *0.006 |
| $A_{420}$ | *0.006 | *0.008 |

*Standard Deviation (Absorbance units/cm optical pathlength) for measurement of a single well. Data taken with 200 µl sample volumes in a quartz 96 well microplate in a SPECTRAmax ® Plus microplate spectrophotometer. N = 96. Mean pathlength = 0.522 cm. Mean $A_{420}$ and $(A_{420}-A_{520})$ per cm pathlength = 0.380.

The difference in absorbance at 1000 and 900 nanometers was used to compute the optical pathlength through the aqueous test analyte solution. As shown in FIGS. 5 and 6, the absorbance of solvent in dilute aqueous solutions of analytes is substantially independent of temperature within 20 nanometers of the temperature isosbestic wavelength near 1000 nanometers; within 40 nanometers of another temperature isosbestic wavelength near 1110 nanometers; and in the region of 750 to 940 nanometers encompassing the temperature isosbestic wavelength near 920 nanometers. The difference in absorbance between any two temperature isosbestic wavelength regions may be utilized for monitoring the pathlength of the solvent. The temperature isosbestic points near 1000 and 920 nanometers were selected to determine the optical pathlength through the aqueous test analyte solution because the difference in absorbance for any given optical pathlength is greatest with these two wavelengths, yet these two wavelength values all relatively close, one to another. Further, it is advantageous to select the wavelengths to be as long as possible to a) minimize possible interference from substances which absorb strongly in the visible wavelengths and b) minimize interferences from light scattering phenomena (e.g. Raleigh Scattering, which is inversely proportional to wavelength raised to the fourth power).

As a consequence of selecting a temperature isosbestic wavelength and not wavelength at an absorbance maximum or minimum, the slope of change in absorbance with change in wavelength is quite large. Wavelength selection precision, thus is very important for reproducibly and accurately measuring optical pathlength. Further accuracy is realized when all channels of a multi-channel vertical-beam photometer are exactly matched, or alternatively, separately calibrated. The following example shows that additional precision may be obtained by separately calibrating each channel of a multiple-(8) channel microplate spectrophotometer.

2. Separate calibration of each optical channel of a vertical-beam photometer may be performed by placing a cuvette of constant optical pathlength in each channel the sample compartment of a vertical-beam photometer and separately measuring the differential absorbance of sample solvent (in this case water) in each channel. For example $(A_{1000}-A_{900})$ may be measured for water in a 1 cm pathlength cuvette. The differential absorbance values measured respectively for each optical channel are stored and subsequently recalled to calculate optical pathlength from differential absorbance values measured on aqueous samples of unknown optical pathlength.

Alternatively, separate calibration of each optical channel may be performed by employing a horizontal-beam reference cuvette (as shown in FIG. 10) and measuring the absorbance of an analyte dissolved in a reference solution which is contained in the reference cuvette. (This is called the reference analyte calibration method.) In this measurement, absorbance by the cuvette containing a reference solvent (without the reference analyte) is subtracted from the absorbance value taken with the reference analyte dissolved in the reference solvent to obtain a calibration absorbance value for the reference analyte. Next, the same reference solution is placed into the sample wells of a multi-assay plate in a housing enclosing the multi-assay plate in the optical path of the vertical-beam photometer. Again, absorbance of the multi-assay plate containing a reference solvent (without the reference analyte) is subtracted from the absorbance values taken with the reference analyte dissolved in the reference solvent to obtain a calibration absorbance value for the reference analyte in the multi-assay plate. In addition, differential absorbance of the sample solvent is measured in each channel. For example, $(A_{1000}-A_{900})$ may be measured when the sample solvent is water. This measurement is repeated with the same reference solution for each optical channel of the vertical-beam photometer. From the results of reference analyte absorbance and differential absorbance of the sample solvent in each channel, a calibration value is calculated for each optical channel so that the absorbance of the analyte per unit optical pathlength for each vertical-beam photometer channel is identical to the result obtained in the reference cuvette.

The reference analyte calibration method described above was applied to each channel of a SPECTRAmax®PLUS microplate spectrophotometer. Next error analysis for determination of Analyte Absorbance per Unit Optical Pathlength was determined for the same analyte, under similar conditions as were used to generate the data shown in Table IV. Analyte absorbance was measured as $(A_{420}-A_{520})$ under conditions giving optimal precision. When an average calibration value was used for all 8 channels of the vertical-beam photometer a standard deviation of 0.0021 (0.55% coefficient of variation) was observed. When eight (8) separately-determined calibration values were used for the respective 8 channels of the SPECTRAmax®PLUS microplate spectrophotometer, a standard deviation of 0.0011 (0.29% coefficient of variation) was observed. In each case, the results were the mean of 3 multi-assay plates, each containing 96 samples (N=288). Thus, measurement precision was approximately doubled by employing solvent pathlength calibration values individually determined for each optical channel.

EXAMPLE 12

Measurement of Solvent Absorbance at NIR
Wavelengths Greater than 1100 Nanometers.

In vertical-beam photometry, optical pathlengths generally vary from about 0.05 cm to about 2.0 cm. Most frequently the sample volumes are between 2 millimeters and 1.0 cm. For precise analysis of Analyte Absorbance per Unit Optical Pathlength on very small sample volumes, precise measurement of Optical Pathlength on short pathlengths between 0.05 cm and 0.5 cm is advantageous. As shown in FIGS. 5–8, the differential absorbance of aqueous solutions, at any two wavelengths between 750 nanometers and 1100 nanometers is less than 0.2 for a 1 cm pathlength. For a 0.1 cm pathlength, for example, this results in a differential absorbance less than 0.020. The precision of individual absorbance measurements in vertical-beam photometers is generally about 0.001 absorbance units. Thus, significant error (in this case about 7% coefficient of variation) will be inherent in measurement of 0.1 cm optical pathlengths in aqueous solutions. Increasing the amplitude of absorption of the solvent, or alternatively, increasing the precision of absorbance measurements is necessary to improve analytical precision.

The amplitude of the absorbance of solvents generally employed in analytical chemistry, such as alcohols, ketones, aromatic hydrocarbons (e.g. benzenes, toluenes and anilines), alkanes, furans, sulfoxides, as well as aqueous media, are generally quite small in the region between 770 nanometers and 1100 nanometers. The amplitude of absorbance of these solvents increases at wavelengths longer than 1100 nanometers. These wavelengths generally will be within the near infrared region (750–2500 nm wavelength) or the infrared region of the electromagnetic spectrum (2.5 micron to 1000 micron wavelength).

Analyte Absorbance, Optical Pathlength and Analyte Absorbance per Unit Optical Pathlength of three different analytes (at three different analyte analysis wavelengths) were determined by vertical-beam photometry. In each case, optical pathlength by measuring light absorption by a sample solvent is determined both at temperature isosbestic wavelengths less than 1100 nanometers and at temperature isosbestic wavelengths greater than 1100 nanometers. For wavelengths less than 1100 nm, differential absorbance of water at the temperature isosbestic wavelengths of 900 and 1000 nanometers preferably is used to determine solvent pathlength (as described above). For wavelengths greater than 1100 nm, differential absorbance of water at the temperature isosbestic wavelengths of 1100 and 1200 nanometers preferably is used to determine solvent pathlength. For absorbance measurements employing wavelengths longer than 1100 nanometers, the silicon photodetectors (both the reference and sample measurement silicon photodiodes) in one optical channel of a SPECTRAmax®PLUS vertical-beam spectrophotometer (1 sample and 1 reference photodetector) were replaced with InGaAs PIN Photodiodes (Type No. G5832-03, obtained from Hamamatsu Corporation, Hamamatsu City, Japan). For comparison purposes, the absorbance of each analyte also was measured in a 1 cm fixed optical pathlength cuvette by horizontal-beam photometry.

The results of the absorbance measurements are summarized in TABLE V. Vertical-beam photometry in each case was performed at 6 different optical pathlengths. The first analyte listed is bovine serum albumin (BSA) at 2 mg/ml in phosphate-buffered saline (0.05 M sodium phosphate, 0.1M NaCl, pH 7.2 (PBS)). Absorbance of the BSA analyte was determined at 280 nm. When analyzed in the 1 cm fixed optical pathlength cuvette, $A_{280}$ was 0.995. When analyzed by vertical-beam photometry employing 900 nm and 1000 nm differential absorbance to determine optical pathlength of the PBS solvent, $A_{280}$ (per cm optical pathlength) ranged from 1.033, at 350 μl sample volume, to 1.054 at 100 μl sample volume. The later value is 5.9% greater than the 0.995 $A_{280}$ reference value determined in the 1.0 cm fixed pathlength cuvette. In contrast, when analyzed by vertical-beam photometry employing 1200 nm and 1100 nm differential absorbance to determine optical pathlength of the PBS solvent, $A_{280}$ (per cm optical pathlength) ranged from 1.007, at 350 μl sample volume, to 1.017 at 100 μl sample volume. The later value is only 2.2% greater than the 0.995 $A_{280}$ reference value. Thus, the accuracy at the 100 μl sample volume was substantially improved by employing 1200 nm and 1100 nm differential absorbance to determine optical pathlength of the PBS solvent.

The second analyte shown in TABLE V was yellow food coloring in 0.05 M potassium phosphate buffer, adjusted to pH 7.00 with NaOH. The test analyte solution is available from Fisher Scientific as Catalog Number SB107-500 (pH 7.00 Buffer Solution). Absorbance of the yellow food coloring analyte was determined at 420 nm. When analyzed in the 1 cm fixed optical pathlength cuvette, $A_{420}$ was 0.389. When analyzed by vertical-beam photometry employing 900 nm and 1000 nm differential absorbance to determine optical pathlength of the PBS solvent, $A_{420}$ (per cm optical pathlength) ranged from 0.395 at 350 μl sample volume, to 0.403 at 100 μl sample volume. The later value is 4.0% greater than the 0.389 $A_{420}$ reference value determined in the 1.0 cm fixed pathlength cuvette. In contrast, when analyzed by vertical-beam photometry employing 1200 nm and 1100 nm differential absorbance to determine optical pathlength of the 0.05 M potassium phosphate buffer solvent, $A_{420}$ (per cm optical pathlength) ranged from 0.384, at 350 μl sample volume, to 0.385 at 100 μl sample volume. The later value is only about 0.3% less than the 0.389 $A_{420}$ reference value. Thus, the accuracy at the 100 μl sample volume again is greatly improved by employing 1200 nm and 1100 nm differential absorbance to determine optical pathlength of the PBS solvent.

The third analyte shown in TABLE V was Napthol Green B dye (Aldrich Chemical Co., Milwaukee, Wis.) dissolved in water (50 μg/ml). Absorbance of the Napthol Green B dye analyte was determined at 720 nm. When analysed in the 1 cm fixed optical pathlength cuvette, $A_{720}$ was 0.569. When analysed by vertical-beam photometry employing 900 nm and 1000 nm differential absorbance to determine optical pathlength of the PBS solvent, $A_{720}$ (per cm optical pathlength) ranged from 0.917 at 350 μl sample volume, to 0.904 at 100 μl sample volume. All of these values are approximately 60% greater than the 0.569 $A_{720}$ reference value determined in the 1.0 cm fixed pathlength cuvette. This very large error is attributed to significant differential absorbance of the Napthol Green B dye at 900 and 1000 nanometers. In contrast, when analysed by vertical-beam photometry employing 1200 nm and 1100 nm differential absorbance to determine optical pathlength of the water solvent, $A_{720}$ (per cm optical pathlength) ranged from 0.569, at 350 μl sample volume, to 0.560 at 100 μl sample volume. The later value is about 1.6.% less than the 0.569 $A_{720}$ reference value. Thus, the accuracy at the 100 μl sample volume again is greatly improved by employing 1200 nm and 1100 nm differential absorbance to determine optical pathlength of the (aqueous) solvent. The considerable interference of the Napthol Green B dye is removed by performing the optical pathlength determination at the 1100 and 1200 temperature isosbestic wavelengths of the (aqueous) solvent. In general, employing absorbance measurements at temperature isosbestic wavelengths greater than 1000 nanometers to determine optical pathlength will provide considerable increased accuracy.

TABLE V

Absorbance/(Cm Optical Pathlength)
With Optical Pathlength Measured at Different NIR Wavelengths in Aqueous Samples

| Sample/Wavelength | Solvent Pathlength Wavelengths | Sample Volume in Microplate | | | | | | Absorbance 1 cm Cuvette |
|---|---|---|---|---|---|---|---|---|
| | | 350 μL | 300 μL | 250 μL | 200 μL | 150 μL | 100 μL | |
| BSA, 2 mg/ml | 1200/1100 nm | 1.007 | 1.019 | 1.032 | 1.021 | 1.026 | 1.017 | 0.995 |
| $A_{280\,nm}$ | 1000/900 nm | 1.033 | 1.030 | 1.030 | 1.033 | 1.044 | 1.054 | |
| Fisher pH 7.0 | 1200/1100 nm | 0.384 | 0.386 | 0.386 | 0.385 | 0.385 | 0.385 | 0.389 |
| (yellow) Buffer | 1000/900 nm | 0.395 | 0.396 | 0.398 | 0.398 | 0.396 | 0.403 | |
| $A_{420\,nm}$ | | | | | | | | |
| Napthol Green B, | 1200/1100 nm | 0.569 | 0.571 | 0.577 | 0.566 | 0.573 | 0.560 | 0.569 |
| 50 ug/ml | 1000/900 nm | 0.917 | 0.913 | 0.914 | 0.915 | 0.916 | 0.904 | |
| $A_{720\,nm}$ | | | | | | | | |

From the foregoing it will be appreciated that, although specific embodiments of the invention have been described herein for purposes of illustration, various modifications may be made without deviating from the spirit and scope of the invention.

What is claimed is:

1. A photometric method for measuring light absorption pathlengths of samples of analyte dissolved in water wherein the samples are in wells of a multi-assay plate and where there is an interface between the samples and air comprising determining the sample light absorption pathlength for each of the samples in the wells of the multiassay plate in accordance with the formula:

Sample light absorption pathlength =

$$\text{Reference light absorption pathlength} \times \frac{(A\ smp\ \lambda 1 - Amp\ \lambda 2)}{(A\ ref\ \lambda 1 - A\ ref\ \lambda 2)}$$

wherein (A smp $\lambda_1$ – A smp $\lambda_2$) is the difference in absorptions of light of wavelength $\lambda_1$ and $\lambda_2$ between 700 nanometers and 2500 nanometers which is passed vertically through the samples and to the interface between the samples and air wherein (A ref $\lambda_1$ – A ref $\lambda_2$) is the difference in absorption of light of $\lambda_1$ and $\lambda_2$ passed through a known reference light absorption pathlength.

2. The method of claim 1 wherein the value:

$$\frac{\text{reference light absorption pathlength}}{A\ ref\ \lambda_1 - A\ ref\ \lambda_2}$$

is a predetermined number.

3. The method of claim 1 wherein $\lambda_1$ and $\lambda_2$ are isosbestic wavelengths between 700 nanometers and 2500 nanometers.

4. The method of claim 3 wherein one of the wavelength between 988 and 1008 nanometers and the other wavelength is between 1050 and 1150 nanometers.

5. The method of claim 3 wherein one of the wavelengths is between 998 and 1008 and the other wavelength is between 750 and 930 nanometers.

* * * * *